US008182531B2

(12) United States Patent
Hermans et al.

(10) Patent No.: US 8,182,531 B2
(45) Date of Patent: *May 22, 2012

(54) ACCOMMODATING INTRAOCULAR LENSES AND ASSOCIATED SYSTEMS, FRAMES, AND METHODS

(75) Inventors: Erik Ad Hermans, Amsterdam (NL); Gerrit Ludolph van der Heijde, Muiderberg (NL); Thomas Henricus Marie Terwee, Roden (NL)

(73) Assignee: AMO Groningen B.V., Groningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/006,575

(22) Filed: Jan. 14, 2011

(65) Prior Publication Data
US 2011/0112638 A1    May 12, 2011

Related U.S. Application Data

(63) Continuation of application No. 11/963,118, filed on Dec. 21, 2007, now Pat. No. 7,871,437.

(60) Provisional application No. 60/871,632, filed on Dec. 22, 2006.

(30) Foreign Application Priority Data

Dec. 22, 2006   (EP) ...................................... 06127102
Dec. 12, 2007   (WO) .................. PCT/EP2007/063827

(51) Int. Cl.
*A61F 2/16* (2006.01)
(52) U.S. Cl. ...................... 623/6.38; 623/6.33; 623/6.34; 623/6.32; 623/6.37
(58) Field of Classification Search .................. 623/6.11, 623/6.32, 6.34, 6.37–6.41, 6.43
See application file for complete search history.

(56) References Cited

U.S. PATENT DOCUMENTS

| 1,483,509 | A | 5/1921 | Bugbee |
| 2,129,305 | A | 9/1938 | William |
| 2,274,142 | A | 2/1942 | Houchin |
| 2,405,989 | A | 8/1946 | Beach |
| 2,511,517 | A | 6/1950 | Spiegel |
| 3,031,927 | A | 5/1962 | Wesley |
| 3,034,403 | A | 5/1962 | Neefe |
| RE25,286 | E | 11/1962 | DeCarle |

(Continued)

FOREIGN PATENT DOCUMENTS

AU            3225789 A1    10/1989
(Continued)

OTHER PUBLICATIONS

Adler-Grinberg, Deborah, "Questioning Our Classical Understanding of Accomodation and Presbyopia", American Journal of Optometry & Physiological Optics 1986, 63, 571-580.

(Continued)

*Primary Examiner* — David H Willse
*Assistant Examiner* — Tiffany Shipmon
(74) *Attorney, Agent, or Firm* — AMO Groningen B.V.

(57) ABSTRACT

An intraocular lens for providing accommodative vision to a subject includes a frame disposed about an optical axis, a first optical element, a second optical element, and a connecting element operably coupling the frame to the optical elements. The frame comprises an anterior frame element and a posterior frame element. The connecting element is configured to convert a first displacement between the frame elements in a direction that is substantially parallel to the optical axis into a second displacement between the optical elements that is substantially perpendicular to the optical axis. The second displacement may be translational and/or rotation. In some embodiments, the optical elements are two varifocal lenses.

25 Claims, 20 Drawing Sheets

U.S. PATENT DOCUMENTS

| | | |
|---|---|---|
| 3,210,894 A | 10/1965 | Bentley et al. |
| 3,222,432 A | 12/1965 | Rene |
| 3,227,507 A | 1/1966 | William |
| 3,305,294 A | 2/1967 | Alvarez |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,507,565 A | 4/1970 | Alvarez et al. |
| 3,542,461 A | 11/1970 | Girard et al. |
| 3,583,790 A | 6/1971 | Baker |
| 3,617,116 A | 11/1971 | Jones |
| 3,632,696 A | 1/1972 | Jones |
| 3,693,301 A | 9/1972 | Lemaitre |
| 3,751,138 A | 8/1973 | Humphrey |
| 3,760,045 A | 9/1973 | Thiele et al. |
| 3,827,798 A | 8/1974 | Alvarez |
| 3,922,728 A | 12/1975 | Krasnov |
| 3,932,148 A | 1/1976 | Krewalk, Sr. |
| 3,996,626 A | 12/1976 | Richards et al. |
| 4,055,378 A | 10/1977 | Feneberg et al. |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,426,741 A | 1/1984 | Bittner |
| 4,435,856 A | 3/1984 | L'esperance |
| 4,457,592 A | 7/1984 | Baker |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshore |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,650,292 A | 3/1987 | Baker et al. |
| 4,655,770 A | 4/1987 | Gupta et al. |
| 4,666,445 A | 5/1987 | Tillay |
| 4,676,792 A | 6/1987 | Praeger |
| 4,687,484 A | 8/1987 | Kaplan |
| 4,693,572 A | 9/1987 | Tsuetaki et al. |
| RE32,525 E | 10/1987 | Pannu |
| 4,702,244 A | 10/1987 | Mazzocco |
| 4,704,016 A | 11/1987 | De Carle |
| 4,720,286 A | 1/1988 | Bailey et al. |
| 4,725,278 A | 2/1988 | Shearing |
| 4,731,078 A | 3/1988 | Stoy et al. |
| 4,752,123 A | 6/1988 | Blaker |
| 4,759,762 A | 7/1988 | Grendahl |
| 4,769,033 A | 9/1988 | Nordan |
| 4,780,154 A | 10/1988 | Mori et al. |
| 4,790,847 A | 12/1988 | Woods |
| 4,813,955 A | 3/1989 | Achatz et al. |
| 4,816,031 A | 3/1989 | Pfoff |
| 4,830,481 A | 5/1989 | Futhey et al. |
| 4,842,601 A | 6/1989 | Smith |
| 4,881,804 A | 11/1989 | Cohen |
| 4,883,485 A | 11/1989 | Patel |
| 4,888,012 A | 12/1989 | Horn et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,108,429 A | 4/1992 | Wiley |
| 5,112,351 A | 5/1992 | Christie et al. |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,712 A | 11/1992 | Portney |
| 5,171,266 A | 12/1992 | Wiley et al. |
| 5,171,320 A | 12/1992 | Nishi |
| 5,172,723 A | 12/1992 | Sturgis |
| 5,192,317 A | 3/1993 | Kalb |
| 5,192,318 A | 3/1993 | Schneider et al. |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,275,623 A | 1/1994 | Sarfarazi |
| 5,326,347 A | 7/1994 | Cumming |
| 5,354,335 A | 10/1994 | Lipshitz et al. |
| 5,358,520 A | 10/1994 | Patel |
| 5,391,202 A | 2/1995 | Lipshitz et al. |
| RE34,998 E | 7/1995 | Langerman |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,503,165 A | 4/1996 | Schachar |
| 5,522,891 A | 6/1996 | Klaas |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,653,754 A | 8/1997 | Nakajima et al. |
| 5,674,282 A | 10/1997 | Cumming |
| 5,682,223 A | 10/1997 | Menezes et al. |
| 5,684,560 A | 11/1997 | Roffman et al. |
| 5,725,576 A | 3/1998 | Fedorov et al. |
| 5,728,155 A | 3/1998 | Anello et al. |

| Patent Number | Date | Inventor |
|---|---|---|
| 5,766,244 A | 6/1998 | Binder |
| 5,769,890 A | 6/1998 | McDonald |
| 5,776,191 A | 7/1998 | Mazzocco |
| 5,776,192 A | 7/1998 | McDonald |
| 5,800,533 A | 9/1998 | Eggleston et al. |
| 5,814,103 A | 9/1998 | Lipshitz et al. |
| 5,824,074 A | 10/1998 | Koch |
| 5,876,442 A | 3/1999 | Lipshitz et al. |
| 5,928,283 A | 7/1999 | Gross et al. |
| 5,968,094 A | 10/1999 | Werblin et al. |
| 5,984,962 A | 11/1999 | Anello et al. |
| 6,013,101 A | 1/2000 | Israel |
| 6,051,024 A | 4/2000 | Cumming |
| 6,096,078 A | 8/2000 | McDonald |
| 6,106,554 A | 8/2000 | Bretton |
| 6,113,633 A | 9/2000 | Portney |
| 6,117,171 A | 9/2000 | Skottun |
| 6,120,538 A | 9/2000 | Rizzo, III et al. |
| 6,136,026 A | 10/2000 | Israel |
| 6,176,878 B1 | 1/2001 | Gwon et al. |
| 6,197,058 B1 | 3/2001 | Portney |
| 6,197,059 B1 | 3/2001 | Cumming |
| 6,200,342 B1 | 3/2001 | Tassignon |
| 6,217,612 B1 | 4/2001 | Woods |
| 6,231,603 B1 | 5/2001 | Lang et al. |
| 6,238,433 B1 | 5/2001 | Portney |
| 6,258,123 B1 | 7/2001 | Young et al. |
| 6,277,146 B1 | 8/2001 | Peyman et al. |
| 6,280,471 B1 | 8/2001 | Peyman et al. |
| 6,299,641 B1 | 10/2001 | Woods |
| 6,322,589 B1 | 11/2001 | Cumming |
| 6,327,772 B1 | 12/2001 | Zadno-Azizi et al. |
| 6,342,073 B1 | 1/2002 | Cumming et al. |
| 6,358,280 B1 | 3/2002 | Herrick |
| 6,387,126 B1 | 5/2002 | Cumming |
| 6,406,494 B1 | 6/2002 | Laguette et al. |
| 6,423,094 B1 | 7/2002 | Sarfarazi |
| 6,443,985 B1 | 9/2002 | Woods |
| 6,450,642 B1 | 9/2002 | Jethmalani et al. |
| 6,454,802 B1 | 9/2002 | Bretton et al. |
| 6,464,725 B2 | 10/2002 | Skottun |
| 6,478,821 B1 | 11/2002 | Laguette et al. |
| 6,485,516 B2 | 11/2002 | Boehm |
| 6,488,708 B2 | 12/2002 | Sarfarazi |
| 6,494,911 B2 | 12/2002 | Cumming |
| 6,503,276 B2 | 1/2003 | Lang et al. |
| 6,524,340 B2 | 2/2003 | Israel |
| 6,533,813 B1 | 3/2003 | Lin et al. |
| 6,547,822 B1 | 4/2003 | Lang |
| 6,551,354 B1 | 4/2003 | Ghazizadeh et al. |
| 6,554,859 B1 | 4/2003 | Lang et al. |
| 6,558,420 B2 | 5/2003 | Green |
| 6,598,606 B2 | 7/2003 | Terwee et al. |
| 6,599,317 B1 | 7/2003 | Weinschenk, III et al. |
| 6,616,691 B1 | 9/2003 | Tran |
| 6,616,692 B1 | 9/2003 | Glick et al. |
| 6,638,305 B2 | 10/2003 | Laguette |
| 6,638,306 B2 | 10/2003 | Cumming |
| 6,645,246 B1 | 11/2003 | Weinschenk, III et al. |
| 6,660,035 B1 | 12/2003 | Lang et al. |
| 6,695,881 B2 | 2/2004 | Peng et al. |
| 6,749,634 B2 | 6/2004 | Hanna |
| 6,761,737 B2 | 7/2004 | Zadno-Azizi et al. |
| 6,764,511 B2 | 7/2004 | Zadno-Azizi et al. |
| 6,767,363 B1 | 7/2004 | Bandhauer et al. |
| 6,786,934 B2 | 9/2004 | Zadno-Azizi et al. |
| 6,818,017 B1 | 11/2004 | Shu |
| 6,818,158 B2 | 11/2004 | Pham et al. |
| 6,846,326 B2 | 1/2005 | Zadno-Azizi et al. |
| 6,858,040 B2 | 2/2005 | Nguyen et al. |
| 6,884,261 B2 | 4/2005 | Zadno-Azizi et al. |
| 6,884,263 B2 | 4/2005 | Valyunin et al. |
| 6,899,732 B2 | 5/2005 | Zadno-Azizi et al. |
| 6,926,736 B2 | 8/2005 | Peng et al. |
| 7,018,409 B2 | 3/2006 | Glick et al. |
| 7,025,783 B2 | 4/2006 | Brady et al. |
| 7,041,134 B2 | 5/2006 | Nguyen et al. |
| 7,087,080 B2 | 8/2006 | Zadno-Azizi et al. |
| 7,097,660 B2 | 8/2006 | Portney |
| 7,118,596 B2 | 10/2006 | Zadno-Azizi et al. |
| 7,118,597 B2 | 10/2006 | Miller et al. |
| 7,125,422 B2 | 10/2006 | Woods et al. |
| 7,150,759 B2 | 12/2006 | Paul et al. |
| 7,198,640 B2 | 4/2007 | Nguyen |
| 7,220,279 B2 | 5/2007 | Nun |
| 7,223,288 B2 | 5/2007 | Zhang et al. |
| 7,226,478 B2 | 6/2007 | Ting et al. |
| 7,238,201 B2 | 7/2007 | Portney et al. |
| 7,452,362 B2 | 11/2008 | Zadno-Azizi et al. |
| 7,452,378 B2 | 11/2008 | Zadno-Azizi et al. |
| 7,615,056 B2 | 11/2009 | Ayton et al. |
| 7,645,300 B2 | 1/2010 | Tsai |
| 7,662,180 B2 | 2/2010 | Paul et al. |
| 7,744,603 B2 | 6/2010 | Zadno-Azizi et al. |
| 7,744,646 B2 | 6/2010 | Zadno-Azizi et al. |
| 2001/0001836 A1 | 5/2001 | Cumming |
| 2002/0002404 A1 | 1/2002 | Sarfarazi |
| 2002/0004682 A1 | 1/2002 | Zhou et al. |
| 2002/0045937 A1 | 4/2002 | Sarfarazi |
| 2002/0095212 A1 | 7/2002 | Boehm |
| 2002/0103536 A1 | 8/2002 | Landreville et al. |
| 2002/0107568 A1 | 8/2002 | Zadno-Azizi et al. |
| 2002/0111678 A1 | 8/2002 | Zadno-Azizi et al. |
| 2002/0116057 A1 | 8/2002 | Ting et al. |
| 2002/0116058 A1 | 8/2002 | Zadno-Azizi et al. |
| 2002/0116060 A1 | 8/2002 | Nguyen et al. |
| 2002/0116061 A1 | 8/2002 | Zadno-Azizi et al. |
| 2002/0120329 A1 | 8/2002 | Lang et al. |
| 2002/0138140 A1 | 9/2002 | Hanna |
| 2002/0143395 A1 | 10/2002 | Skottun |
| 2002/0161434 A1 | 10/2002 | Laguette et al. |
| 2002/0193876 A1 | 12/2002 | Lang et al. |
| 2003/0002404 A1 | 1/2003 | Maekawa |
| 2003/0018384 A1 | 1/2003 | Valyunin et al. |
| 2003/0033013 A1 | 2/2003 | Callahan et al. |
| 2003/0050695 A1 | 3/2003 | Lin et al. |
| 2003/0050696 A1 | 3/2003 | Cumming |
| 2003/0050697 A1 | 3/2003 | Paul |
| 2003/0060881 A1 | 3/2003 | Glick et al. |
| 2003/0078657 A1 | 4/2003 | Zadno-Azizi et al. |
| 2003/0078658 A1 | 4/2003 | Zadno-Azizi |
| 2003/0083744 A1 | 5/2003 | Khoury |
| 2003/0093149 A1 | 5/2003 | Glazier |
| 2003/0105522 A1 | 6/2003 | Glazier |
| 2003/0109925 A1 | 6/2003 | Ghazizadeh et al. |
| 2003/0114927 A1 | 6/2003 | Nagamoto |
| 2003/0130732 A1 | 7/2003 | Sarfarazi |
| 2003/0149480 A1 | 8/2003 | Shadduck |
| 2003/0158599 A1 | 8/2003 | Brady et al. |
| 2003/0187504 A1 | 10/2003 | Weinschenk et al. |
| 2003/0187505 A1 | 10/2003 | Liao |
| 2003/0204254 A1 | 10/2003 | Peng et al. |
| 2003/0204255 A1 | 10/2003 | Peng et al. |
| 2004/0015236 A1 | 1/2004 | Sarfarazi |
| 2004/0039446 A1 | 2/2004 | McNicholas |
| 2004/0082993 A1 | 4/2004 | Woods |
| 2004/0082994 A1 | 4/2004 | Woods et al. |
| 2004/0111153 A1 | 6/2004 | Woods et al. |
| 2004/0148023 A1 | 7/2004 | Shu |
| 2004/0158322 A1 | 8/2004 | Shen |
| 2004/0162612 A1 | 8/2004 | Portney et al. |
| 2004/0167621 A1 | 8/2004 | Peyman |
| 2004/0215340 A1 | 10/2004 | Messner et al. |
| 2004/0230300 A1 | 11/2004 | Bandhauer et al. |
| 2004/0249456 A1 | 12/2004 | Cumming |
| 2005/0027354 A1 | 2/2005 | Brady et al. |
| 2005/0049700 A1 | 3/2005 | Zadno-Azizi et al. |
| 2005/0055092 A1 | 3/2005 | Nguyen et al. |
| 2005/0060032 A1 | 3/2005 | Magnante et al. |
| 2005/0085906 A1 | 4/2005 | Hanna |
| 2005/0085907 A1 | 4/2005 | Hanna |
| 2005/0113914 A1 | 5/2005 | Miller et al. |
| 2005/0125057 A1 | 6/2005 | Cumming |
| 2005/0125058 A1 | 6/2005 | Cumming et al. |
| 2005/0131535 A1 | 6/2005 | Woods |
| 2005/0137703 A1 | 6/2005 | Chen |
| 2005/0228401 A1 | 10/2005 | Zadno-Azizi et al. |
| 2005/0234547 A1 | 10/2005 | Nguyen et al. |

| | | | |
|---|---|---|---|
| 2005/0267575 A1 | 12/2005 | Nguyen et al. | |
| 2006/0064162 A1 | 3/2006 | Klima | |
| 2006/0100703 A1 | 5/2006 | Evans et al. | |
| 2006/0111776 A1 | 5/2006 | Glick et al. | |
| 2006/0178741 A1 | 8/2006 | Zadno-Azizi et al. | |
| 2006/0184244 A1 | 8/2006 | Nguyen et al. | |
| 2006/0209430 A1 | 9/2006 | Spivey | |
| 2006/0209431 A1 | 9/2006 | Spivey | |
| 2006/0238702 A1 | 10/2006 | Glick et al. | |
| 2006/0259139 A1 | 11/2006 | Zadno-Azizi et al. | |
| 2006/0271187 A1 | 11/2006 | Zadno-Azizi et al. | |
| 2007/0027540 A1 | 2/2007 | Zadno-Azizi et al. | |
| 2007/0050025 A1 | 3/2007 | Nguyen et al. | |
| 2007/0078515 A1 | 4/2007 | Brady | |
| 2007/0106377 A1 | 5/2007 | Smith et al. | |
| 2007/0108643 A1 | 5/2007 | Zadno-Azizi et al. | |
| 2008/0125790 A1 | 5/2008 | Tsai et al. | |
| 2010/0057203 A1 | 3/2010 | Glick et al. | |

FOREIGN PATENT DOCUMENTS

| | | | |
|---|---|---|---|
| DE | 2702117 A1 | 7/1978 | |
| DE | 3246306 A1 | 6/1984 | |
| DE | 19501444 A1 | 7/1996 | |
| DE | 10125829 A1 | 11/2002 | |
| EP | 162573 A2 | 11/1985 | |
| EP | 212616 A2 | 3/1987 | |
| EP | 246216 A2 | 11/1987 | |
| EP | 329981 A1 | 8/1989 | |
| EP | 331457 A2 | 9/1989 | |
| EP | 336877 A1 | 10/1989 | |
| EP | 0337390 A2 | 10/1989 | |
| EP | 337390 A3 | 10/1989 | |
| EP | 342895 A2 | 11/1989 | |
| EP | 351471 A2 | 1/1990 | |
| EP | 420549 A2 | 4/1991 | |
| EP | 566170 A1 | 10/1993 | |
| EP | 691109 A1 | 1/1996 | |
| EP | 779063 A1 | 6/1997 | |
| EP | 897702 A2 | 2/1999 | |
| EP | 1321112 A1 | 6/2003 | |
| EP | 1647241 A2 | 4/2006 | |
| GB | 2058391 A | 4/1981 | |
| GB | 2124500 A | 2/1984 | |
| GB | 2129155 A | 5/1984 | |
| GB | 2146791 A | 4/1985 | |
| GB | 2192291 A | 1/1988 | |
| GB | 2215076 A | 9/1989 | |
| JP | 2126847 A2 | 5/1990 | |
| JP | 7222760 A2 | 8/1995 | |
| JP | 9501856 T2 | 2/1997 | |
| JP | 2003190193 A | 7/2003 | |
| RU | 2014038 C1 | 6/1994 | |
| RU | 2014039 C1 | 6/1994 | |
| WO | WO8404449 A1 | 11/1984 | |
| WO | WO8603961 A1 | 7/1986 | |
| WO | WO8700299 A1 | 1/1987 | |
| WO | WO8707496 A1 | 12/1987 | |
| WO | WO8902251 A1 | 3/1989 | |
| WO | WO8911672 A1 | 11/1989 | |
| WO | WO9302639 A1 | 2/1993 | |
| WO | WO9416648 A1 | 8/1994 | |
| WO | WO9503783 A1 | 2/1995 | |
| WO | WO9615734 A2 | 5/1996 | |
| WO | WO9625126 A1 | 8/1996 | |
| WO | WO9743984 A1 | 11/1997 | |
| WO | WO9903427 A1 | 1/1999 | |
| WO | WO9920206 A1 | 4/1999 | |
| WO | WO0021467 A1 | 4/2000 | |
| WO | WO0027315 A1 | 5/2000 | |
| WO | WO0061036 A1 | 10/2000 | |
| WO | WO0066037 A1 | 11/2000 | |
| WO | WO0066040 A1 | 11/2000 | |
| WO | WO0119288 A1 | 3/2001 | |
| WO | WO0119289 A1 | 3/2001 | |
| WO | WO0134067 A1 | 5/2001 | |
| WO | WO0164136 A2 | 9/2001 | |
| WO | WO0166042 A1 | 9/2001 | |
| WO | WO0219949 A2 | 3/2002 | |
| WO | WO02071983 A1 | 9/2002 | |
| WO | WO03009051 A2 | 1/2003 | |
| WO | WO03015657 A2 | 2/2003 | |
| WO | WO03057081 A2 | 7/2003 | |
| WO | WO03059196 A2 | 7/2003 | |
| WO | WO03059208 A2 | 7/2003 | |
| WO | WO03084441 A1 | 10/2003 | |
| WO | WO03092552 A1 | 11/2003 | |
| WO | WO2004000171 A1 | 12/2003 | |
| WO | WO2004073559 A1 | 9/2004 | |
| WO | WO2005084587 A2 | 9/2005 | |
| WO | WO2006025726 A1 | 3/2006 | |
| WO | WO2006118452 A1 | 11/2006 | |
| WO | WO2007067872 A2 | 6/2007 | |
| WO | WO200807967 A1 | 7/2008 | |
| WO | WO2008077795 A2 | 7/2008 | |

OTHER PUBLICATIONS

Alcon Surgical, Alcon Laboratories, No Date Given.
Arno Specs Model AC-21B, 1992.
Chauvin-Opsia, Azurite ACL(0459) No Date Given.
Chiron. Clemente Optifit Modell SPSP525 Brochure Translation. Dec. 1998.
Chiron Vision, Nuvita Mar. 20, 1997 (Chiron Vision Corp. 1997), 6 pages.
Fechner P.U., et al., "Iris-Claw Lens in Phakic Eyes to Correct Hyperopia: Preliminary Study," Journal of Cataract and Refractive Surgery, 1998, vol. 24 (1), pp. 48-56.
"Hanita Lenses, Ocular Surgery News Int'l, No Date Given".
Internation Search Report for the Application No. PCT/EP2007/063827 mailed on Oct. 5, 2010.
Iolab Corp. Opthalmology Times. Mar. 15, 1995.
"Mediphacos Ltd. Ocular Surgery News Int'l No date given".
Menezo J.L., et al., "Endothelial Study of Iris-Claw Phakic Lens: Four Year Follow-Up," Journal of Cataract Refractive Surgery, 1998, vol. 24 (8), pp. 1039-1049.
Opthamed Inc, Omac-260, No Date Given.
U.S. Appl. No. 09/656,661, filed Sep. 7, 2000.
Simonov A.N., et al., "Cubic Optical Elements for an Accommodative Intraocular Lens," Optics Express, 2006, vol. 14 (17), pp. 7757-7775.
"Storz. Opthalmics Inc. Model LIZZUV ACL. No date given".
Tetz M., et al., "Evaluating and Defining the Sharpness of Intraocular Lenses: Part 1: Influence of Optic Design on the Growth of the Lens Epithelial Cells in Vitro," Journal of Cataract and Refractive Surgery, 2005, vol. 31 (11), pp. 2172-2179.
Thornton S., "Accommodation in Pseudophakia," 1991, pp. 159-162.
Tsutomu Hara et al, "Accommodative Intraocular Lens with Spring Action Part 1 Design and Placement in an Excised Animal Eye," Ophthalmic Surgery, pp. 128-133, 1990, vol. 21.
"Universe IOL Center, Ocular Surgery News Int'l, No Date Given".
U.S. Appl. No. 09/721,072, filed Nov. 22, 2000.
"World optics Inc ophthalmology times Mar. 15, 1995,".

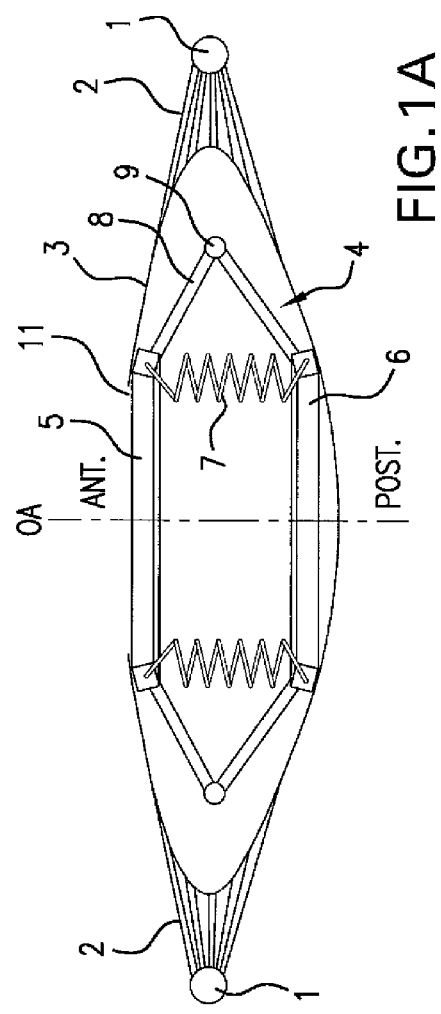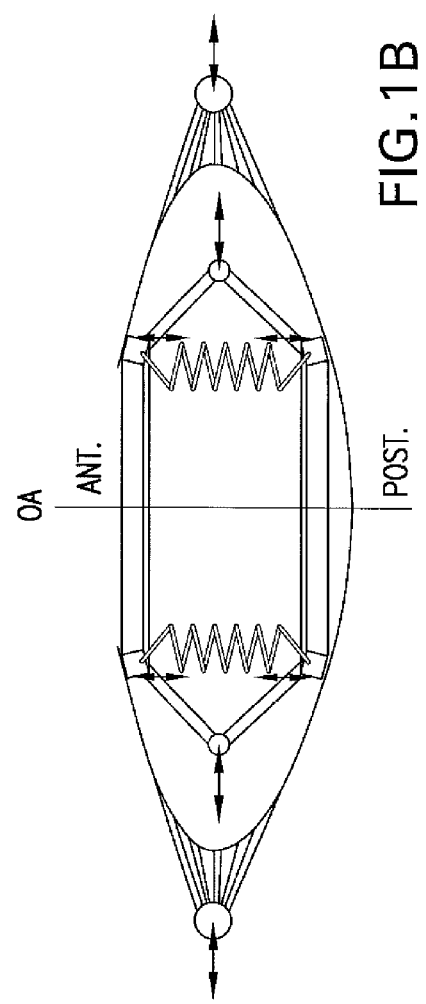

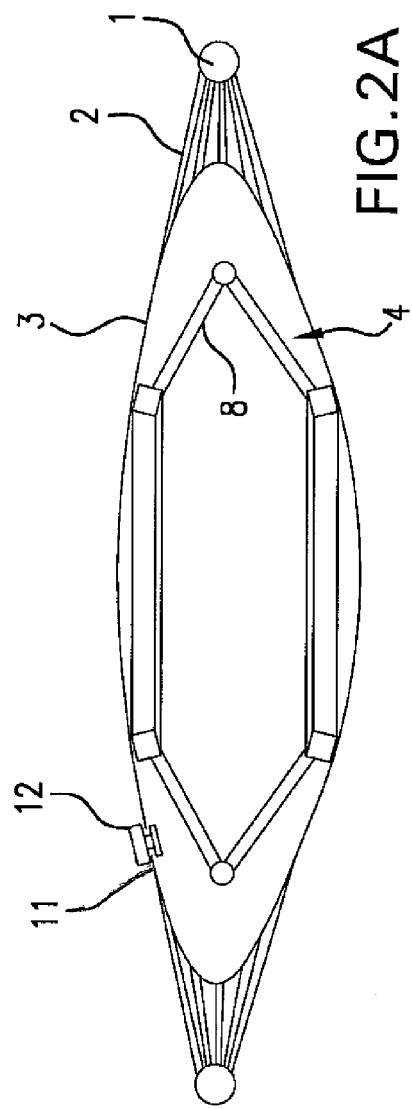
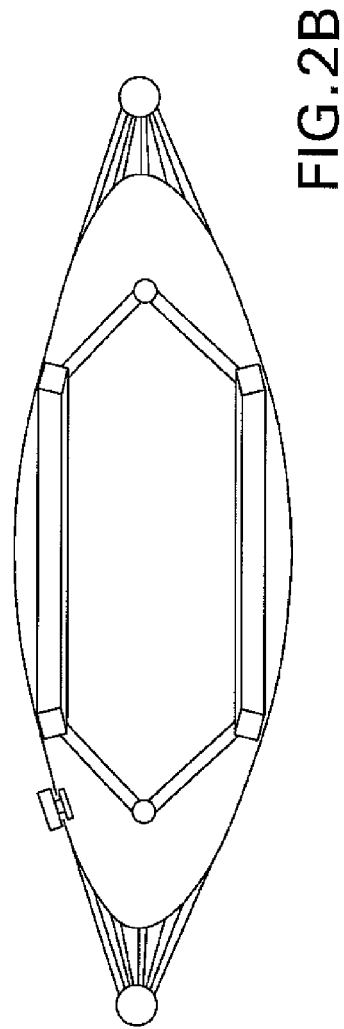
FIG.2A
FIG.2B

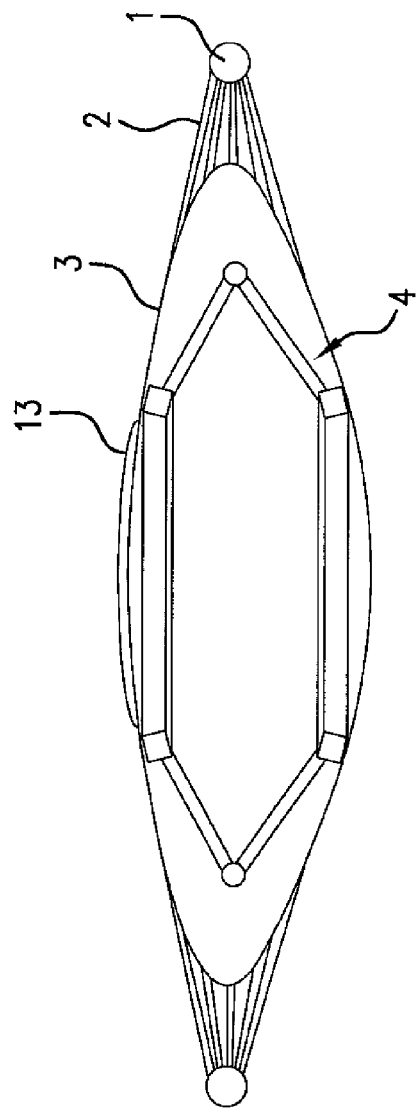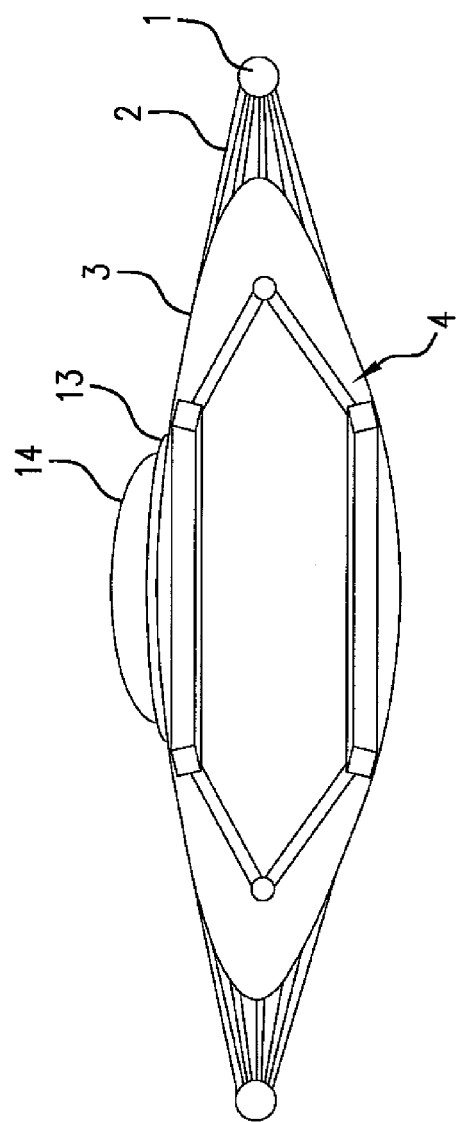

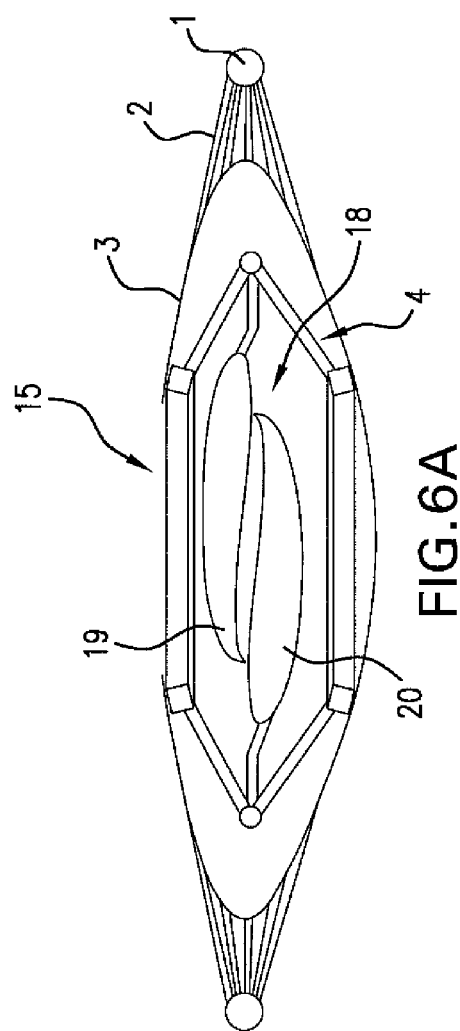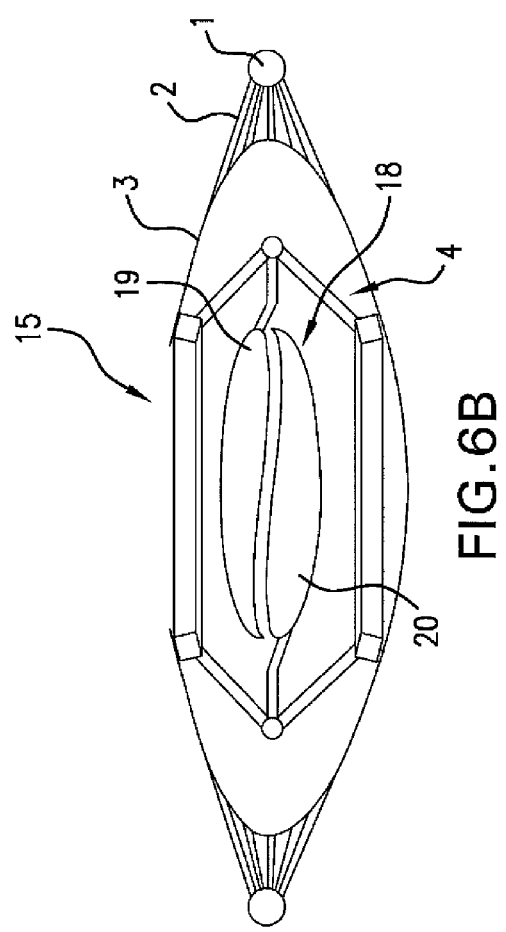

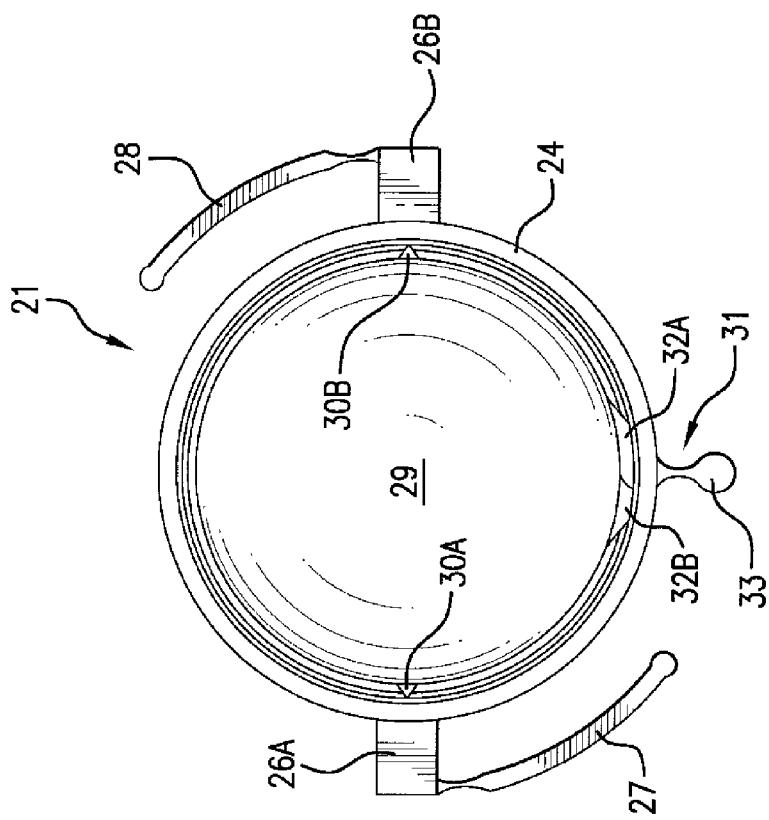
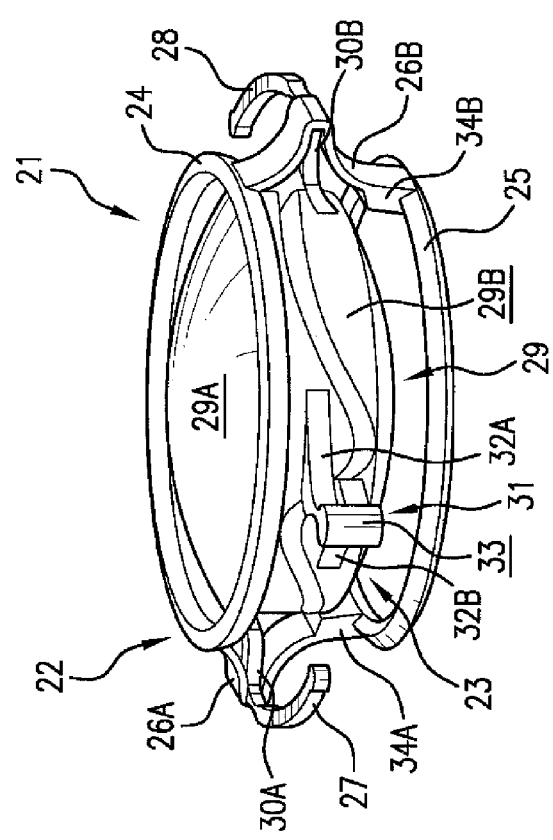
FIG.8
FIG.7

ACCOMMODATING INTRAOCULAR LENSES AND ASSOCIATED SYSTEMS, FRAMES, AND METHODS

RELATED APPLICATIONS

The present application is a continuation of application U.S. Ser. No. 11/963,118 filed on Dec. 21, 2007, which claims priority under 35 U.S.C. §119(e) to provisional application No. 60/871,632, filed on Dec. 22, 2006, to European application no. 06127102.9 filed on Dec. 22, 2006, and to PCT application no. PCT/EP2007/063827, filed on 12 Dec. 2007.

BACKGROUND OF THE INVENTION

1. Field of the Invention

The present invention relates generally to intraocular lenses and more specifically to accommodating intraocular lenses.

2. Description of the Related Art

In a natural eye, the accommodative power, i.e. the ability to (dynamically) vary the focal length of the lens and thus of the eye as a whole, is provided by the reversible deformation of the lens between more and less curved shapes. The natural lens comprises a crystalline lens in a lens capsule or capsular bag. The capsular bag is connected to the so-called zonulae. The zonulae extend generally radially from the lens and are connected with their other end to the ciliary muscle which surrounds the eye essentially in the equatorial plane. The natural lens is generally resilient and strives to a generally more spherical shape.

In the relaxed state of the ciliary muscle its diameter is relatively wide. This causes the zonulae to pull on the capsular bag and to flatten the lens against its resilience. In a young, healthy human eye without refractive errors, this causes the eye to become emmetropic, i.e. having acute vision in "infinity" in a desaccommodated state. Emmetropy is usually determined by having a patient read a predetermined line of an eye-chart from a distance of approximately 5 meters.

When the ciliary muscle contracts, its inner diameter reduces, thus reducing the tension in the zonulae. As a consequence, the natural lens relaxes to assume a shape with a stronger curvature. Thus, the focal power of the lens is increased and the eye can focus on shorter distances, e.g. for reading.

Due to aging or an affliction, the natural lens may lose some or substantially all of its resiliency and only allow accommodation over a limited scope, e.g. resulting in age-related farsightedness or presbyopia.

Several optical surgery procedures, e.g. cataract surgery, involve the removal of the natural crystalline lens of an eye. In order to install or restore vision to the patient after such surgery an artificial lens may be implanted in the eye. Presently, most implanted artificial lenses have a fixed focal length or are multi-focal lenses having two or more fixed focal lengths. These lens types provide no or at most pseudo-accommodative power. This leaves patients who have underwent such surgery more or less handicapped in everyday life, since they are no longer able to quickly and rapidly focus at any given distance.

When the natural crystalline lens is surgically removed from the lens capsule, the capsular bag may be left essentially intact, in that it can still be deformed by the ciliary muscle if a sufficient counterforce is provided. This functionality can remain even when a substantial window, or rhexis, has been cut out of the capsular bag.

There is thus ongoing research for an artificial intraocular lens or lens system providing accommodative power, especially by using the natural focussing system of the eye, relying on the reversible deformation of the lens, and a number of patent applications and patents discuss accommodating intraocular lenses.

For instance, U.S. Pat. No. 4,994,082, US and 2004/0158322 discuss complex lens systems mounted in a frame wherein the individual lenses move with respect to each other essentially in a plane perpendicular to the optical axis. U.S. Pat. No. 4,994,082 also discusses displacing two lenses along the optical axis.

Furthermore, U.S. Pat. No. 5,275,623, US 2002/0116061, US 2004/0082994 and US 2005/055092 discuss an accommodating intraocular lens comprising a frame and two lenses which are displaced along the optical axis of the lens system and of the eye, wherein the relative motion of the anterior and posterior parts of the capsular bag is used for realising the motion of the lenses.

US 2005/0131535 discusses a deformable intraocular lens in a frame.

It should be noted that U.S. Pat. No. 3,305,294 U.S. Pat. No. 3,507,565, U.S. Pat. No. 3,583,790, U.S. Pat. No. 3,617,116, U.S. Pat. No. 3,632,696, U.S. Pat. No. 3,751,138, U.S. Pat. No. 3,827,798 and U.S. Pat. No. 4,457,592 describe changing the focal length of a lens system comprising two particularly shaped lenses by linearly displacing the lenses with respect to each other.

Using such lenses for intraocular lenses is known from WO 2005/084587, WO 2006/025726, WO 2006/118452 and from Simonov A N, Vdovin G, Rombach M C, Opt Expr 2006; 14:7757-7775.

U.S. Pat. No. 4,650,292 discusses rotating optical elements of a compound lens with respect to each other for changing the focal length thereof, using surfaces described by polynomial equations having a non-zero term of at least fourth order.

Further, U.S. Pat. No. 6,598,606 describes a method for providing a lens implant in a lens capsule with a predetermined refractive value.

In all these prior art (intraocular) lenses and lens system relatively large displacements of the lenses with respect to each other are used for accommodating and/or the intraocular lenses use the equatorial motion of the zonulae and/or capsular bag for effecting accommodation.

It has been found that when an artificial lens has been implanted into the capsular bag, the flexibility of the capsular bag, and thus its accommodative power reduces over time, which effect is usually most pronounced around the equatorial rim of the capsular bag.

Further, it has been found that, in time, cellular growth or migration may cause further stiffening of (the remainder of) the capsular bag and opacification thereof, and consequentially not only loss of accommodative power but also general loss of sight to the patient.

SUMMARY OF THE INVENTION

An object of the present invention is to provide improvements for artificial intraocular lenses, in particular for accommodating intraocular lenses. One aspect of the present invention involves intraocular lenses with associated frames or support structures for providing relative motion between at least two optical elements, the relative motion providing a change in focal length or accommodation of the intraocular lenses.

In one embodiment, an intraocular frame for implantation in the capsular bag of an eye comprises an anterior frame element, a posterior frame element, and one or more connecting elements. The frame elements are disposed about an optical axis. The connecting element is configured to operably couple the frame elements to first and second optical elements. The connecting element is further configured to convert a first displacement between the frame elements in a direction that is substantially parallel to the optical axis into a second displacement between the optical elements, the second displacement being substantially perpendicular to the optical axis.

The first displacement is preferably substantially parallel to the optical axis of the eye. The second displacement is preferably substantially perpendicular to the first displacement and substantially perpendicular to the optical axis of the eye.

The frame may also include a resilient element for urging the anterior and posterior frame elements towards a predetermined axial separation. The predetermined axial separation may be chosen such that the anterior and posterior frame elements are urged against the anterior and posterior inner wall, respectively, of the capsular bag when implanted therein.

The resilient element may be configured to bias the anterior and posterior frame elements against the anterior and posterior inner wall, respectively, of the capsular bag when implanted therein. Accordingly, the first displacement of the anterior and posterior frame elements will be caused by the action of the capsular bag under the influence of the ciliary muscle. Such a frame is thus beneficial in that the motion of the capsular bag in the direction of the optical axis is coupled with a motion of an optical element at least partially in a perpendicular direction thereto. Thus, the frame may mimic the resilient behaviour of the natural lens in this respect.

This contrasts other accommodating intraocular lenses, which may either rely on the equatorial motion and/or close contact to the equatorial rim of the capsular bag and the zonulae for moving optical elements in this plane, or which rely on the motion essentially along the optical axis for moving optical elements in the same direction.

The conversion between the first and second displacements may be caused by a mounting element which is configured to be attached, in use, to an optical element and which may rotate, bend or slide etc., e.g. against another part of the frame or against an inner wall of the capsular bag, upon a displacement of the anterior and posterior frame elements with respect to each other having a component parallel to the optical axis of the eye.

In the frame, the resilient element and the connecting element may be the same, thus reducing the complexity of the device.

In an efficient embodiment, the connecting element of the frame is arranged for converting the first displacement into the second displacement.

In this case, the optical element is, in use, attached between and preferably free from the anterior and posterior frame elements so that it may be essentially immovable along the optical axis, or so that its displacement may be essentially solely determined by the connecting element.

The connecting element may be e.g. an axial torsion-spring oriented substantially parallel to the optical axis, which is wound up or down by the first displacement of the anterior and posterior frame elements and which therewith displaces the optical element essentially perpendicular to the optical axis. The spring is preferably symmetric about the connection to the optical element.

In a preferred embodiment, the connecting element has a deflection from a straight connection between the anterior and posterior frame elements. The deflection may be a hinge, a fold or a resilient curve etc. In this manner, a preferred location is provided which will flex or bend etc. and thus be displaced under the influence of the displacement of the anterior and posterior frame elements with respect to each other. The magnitude of the component of the displacement perpendicular to the optical axis is dependent on the position along the connecting element; the element will generally be substantially immobile relative to the frame at or near the connection to the anterior and posterior frame elements, respectively, and be maximum at the hinge, fold or curve. Thus, it is preferred that the connecting element is configured to be attached to an optical element at least near the point of maximum deflection from a straight connection between the anterior and posterior frame elements, where the response to a displacement of the anterior and posterior frame elements is maximised.

The point of maximum deflection may be in the middle of, or at another position along, the length of the connecting element.

In order to cause a substantially radial component to the second displacement, the deflection of the connecting element may have a radial component with respect to the optical axis of the eye.

It is generally preferred that at least the anterior frame element provides an opening for allowing aqueous humor to pass therethrough, preferably for allowing aqueous humor to flow between the anterior chamber of the eye and the interior of the capsular bag. This is considered beneficial, since it is believed that the aqueous humor has healing properties for the capsular bag in that it reduces or even prevents scar-tissue build-up or generally proliferation of cells on the capsular bag, which might lead to opacity of the capsular bag and subsequent loss of vision. It is therefore preferred that also the posterior frame element is provided with such an opening for allowing aqueous humor to pass therethrough. Depending on the optical properties of the frame, the opening is obviously best situated so as not to block vision.

Efficiently, at least the posterior frame element is provided with a relatively sharp edge along the contact region of the frame element with the wall of the capsular bag. A relatively sharp edge or rim, as opposed to a smoothly rounded one, hinders cellular growth or migration which may occur outside the posterior frame element from passing within a perimeter set by the edge, thus reducing or even preventing cellular growth on and subsequent opacification of the inside of the contact region.

The edge or rim may be essentially square- or acute-angled or even be slightly rounded and still exhibit the cell growth blocking effect. Such roundedness of the edge may be determined by the deviation of the edge from a square angle. An edge with a fillet due to polishing resulting a deviation of up to 13.5 micron has been found to effectively obstruct cell migration across the edge. (Tetz M, Wildeck A. Evaluating and defining the sharpness of intraocular lenses. Part 1: influence of optic design on the growth of the lens epithelial cells in vitro. J Cataract Refract Surg, 2005; 31:2172-2179)

The frame may comprise elements for substantially centering the frame about the optical axis of the eye when implanted therein. Such elements, e.g. haptics, preferably exert no or very low pressure against the equatorial rim of the eye, e.g. just sufficient to keep the frame in place.

It has been observed that the loss of resiliency and flexibility of the capsular bag once an intraocular lens has been implanted therein is most pronounced about the equatorial rim. It is the inventors' believe that the stiffening of the capsular bag may be caused in response to the stress exerted on the capsular bag by the implanted lens. Thus, lenses which stretch or tauten the capsular bag in the radial direction and which rely on a variation in the diameter of the capsular bag for accommodation may cause a deterioration of the function of the capsular bag. It may therefore be preferred not to exert such stress. In a preferred embodiment, therefore, the frame, once implanted in the capsular bag of the eye, is only in contact with the interior surface thereof on the anterior and posterior walls thereof and is free from contact with the equatorial rim thereof. In such embodiments the frame may be configured to be free from such contact both in the accommodated and desaccommodated states as well as in any transitional state.

The frame may also comprise different or additional elements, such as protrusions, legs, rings or wings etc. for securing the position of the frame with respect to the capsular bag.

Preferably, with a frame according to an embodiment of the present invention the net effect of the forces on the capsular bag is to generally urge the capsular bag towards the accommodating shape. Thus, the natural resiliency of the eye may be mimicked, which may lead to maintain the natural accommodating effect and efficiency of the eye for longer periods than is found with present intraocular devices.

Within this text, the equatorial rim is considered to be the part of the capsular bag to which the zonulae are attached. In an adult human eye this part usually extends for about 2.5 mm from the equatorial plane which extends through the maximum girth of the capsular bag, both lengths measured along the surface of the capsular bag. The anterior and posterior sections of the capsular bag are considered the parts anterior and posterior of the equatorial rim, respectively.

Another aspect of the present invention is an intraocular lens for implantation in the capsular bag of an eye having an optical axis. The intraocular lens comprises an optical system attached, in use, to a first connecting element of a frame according to an embodiment of the present invention.

The optical system may thus be substantially free from contact to the walls of the capsular bag, which allows aqueous humor to flow essentially unimpeded around the optical system. Thus, the capsular bag may be passivated or appeased, as described before, preventing stiffening and opacification thereof. Further, the aqueous humor may rinse the optical system with every movement or deformation of the capsular bag and/or the optical system, which is thought to reduce the sticking of cells to the surfaces of the optical system and thus clouding it and therewith possibly impairing vision. In addition, the optical system may be displaced in response to the displacement of the anterior and posterior frame elements and the capsular bag, respectively, which may be used for accommodation.

The optical system is preferably additionally attached, in use, to at least a second connecting element of the frame, so that the position and/or displacement of the optical system is better and more robustly defined and maintained than in the case the system is attached to a single point.

In a beneficial embodiment of the present invention, the optical system is reversibly deformable by the displacement of at least one of the parts thereof which is attached to a connecting element of the frame. Deforming an optical system usually allows to modify its optical properties. Thus, the intraocular lens according to an embodiment of the present invention may be an accommodating lens.

In this case, it is preferred that the optical system comprises a reversibly deformable lens. This allows to mimic the natural eye quite closely. The equatorial pulling force on the lens capsule of a resilient lens by the zonulae may be replaced by the equatorial pulling by corresponding elements of the frame on the artificial lens. The resiliency of the natural lens which urges the capsule to the accommodating configuration and which is lost upon the removal of the crystalline lens is replaced by that of the artificial lens and/or of the frame. The various resiliencies of the different elements may be chosen or configured so as to emulate the forces of the natural eye.

Another preferred optical system comprises at least two optical elements which are movable with respect to each other. This allows to properly design a particular optical configuration and to predict the effect of a relative displacement of the optical elements with respect to each other. The geometric shape and/or material of the optical elements, preferably lenses, may be chosen at will so as to achieve a desired effect.

It is preferred that the at least two optical elements are mutually movably interconnected, so that the relative position and/or motion of the elements may be better defined than generally possible without the interconnection.

The interconnection may provide a centre of rotation for at least two individual optical elements with respect to each other. This allows a well defined rotation of the elements with respect to each other about a common axis.

It is preferred that the optical system comprises at least one resilient element for providing a restoring force for urging the optical system to a default configuration. Thus, the optical system may have a preferred position to which it strives to return. This may increase the similarity of the artificial lens to a natural lens. The default position may be an accommodating position.

The optical system may be provided with at least one element for defining a default configuration. The element may comprise one or more stops for arresting the optical system in this default configuration, or it may be a resilient element having a neutral position etc. This allows definition of a particular optical property, such as a focal length, of the optical system, and to reliably retrieve the configuration for which the property was defined.

This default configuration defined by the at least one element need not be the configuration to which the intraocular lens or the optical system strives; the intraocular lens or the optical system may have a default configuration for achieving emmetropy and one for an accommodated state.

The intraocular lens according to an embodiment of the present invention is preferably arranged so that the net effect of the forces on the capsular bag, at least due to the at least one resilient element of the frame and/or to the at least one resilient element for providing a restoring force for urging the optical system to a default configuration, is to generally urge the capsular bag towards the accommodating shape. Thus the artificial intraocular lens behaves much like the natural lens. The main contribution to the force, either from the frame, the optical system or another element may be chosen, e.g. to suit particular or structural preferences or demands.

According to an aspect of the present invention an intraocular lens is provided comprising a frame and an optical system. The frame comprises an anterior frame element, a posterior frame element, and a first and a second connecting element connecting the anterior and posterior frame elements. The first and second connecting element are configured to be attached, in use, to an optical system. The frame is configured for converting a first displacement of the anterior and posterior frame elements with respect to each other having at least a component parallel to the optical axis of the eye into a second displacement of at least a part of the optical element, the second displacement having at least a component perpendicular to the optical axis of the eye. The optical system is an optical system as disclosed above which is resilient. The net effect of the forces on the capsular bag due to the intraocular lens is to generally urge the capsular bag towards the accommodating shape.

Such an intraocular lens combines the benefits of the embodiments of the intraocular lens discussed above with that of a frame, wherein the frame may be a passive device and need not have a resilient element. The net force of such an intraocular lens may be efficiently optimised, as it originates in the resiliency characteristics of the optical system.

Within this text, a lens may be diffractive, refractive or a combination which may have positive and negative value, but which may also have zero optical strength. Graded index lenses, Fresnel lenses etc. and non-rotationally symmetric lenses, e.g. cylinder lenses, are also included. An optical system may comprise one or more optical elements, wherein each element may be a lens, a lens array, a filter or any other optical element, including opaque devices, mirrors and prisms. Also optical detectors such as bio-compatible CCD- or CMOS-chips are conceivable.

Another aspect of the present invention is an intraocular lens system for implantation in an eye comprising at least two varifocal lenses. In one embodiments, the focal length of the lens system is dependent on at least the rotation of the two lenses with respect to each other about an axis which is substantially parallel to the main optical axis of the lens system and which is substantially stationary with respect to the two lenses. The intraocular lens system further comprises a frame for positioning the lenses into the capsular bag of an eye such that once implanted the main optical axis of the lens system is substantially along the optical axis of the eye. Thus the lens system may be kept in position and preferably its lenses be kept free from contact (or have only limited contact) with the inner wall of the capsular bag. Further, the frame determines and maintains the optical axis of the system to that of the eye, facilitating the lens design.

A combination of varifocal lenses, i.e. lenses which have different foci at different positions on the lens, may provide an optical system exhibiting very large differences in its optical power upon very small relative linear and/or rotational displacements of the constituents. This makes it a preferred optical system for use as an intraocular lens, wherein small displacements are preferred to optimise the ratio thereof to the available volume of the capsular bag.

The frame may be arranged for causing a rotation of the two lenses with respect to each other about an axis which has at least a component parallel to the main optical axis of the lens system, and is preferably substantially parallel thereto, for changing the focal length of the lens system due to the natural action of the ciliary muscle on the capsular bag of the eye. Thus, an accommodating intraocular lens is provided.

Preferably the frame is arranged for causing at least a rotation of the two lenses with respect to each other about an axis which has at least a component parallel to the main optical axis of the lens system and is preferably is substantially parallel thereto due to a displacement of elements of the frame parallel to the optical axis of the eye. Such a frame does not rely on the equatorial motion of the capsular bag of the eye and thus may be free of contact with the equatorial rim thereof, which may reduce the chances of scarring or loss of flexibility of the capsular bag.

The two lenses may be connected with a resilient element which is arranged for causing at least a rotation of the two lenses with respect to each other about an axis which has at least a component parallel to the main optical axis of the lens system and is preferably is substantially parallel thereto to the main optical axis of the lens system for changing the focal length of the lens system due to the natural action of the ciliary muscle on the capsular bag of the eye. A resilient connecting element may urge the lenses to a default position, enabling a well reproducible definition of an optical property of the lens system. A resilient element may also dose the displacement, since it may provide a countering force to the force of the ciliary muscle acting indirectly on the lenses, thus allowing a well-controllable accommodation.

In a preferred embodiment, the two lenses are connected with a resilient element which is arranged for causing at least a rotation of the two lenses with respect to each other about an axis which is substantially parallel to the main optical axis of the lens system due to a displacement of elements of the frame substantially parallel to the optical axis of the eye. Thus allowing to leave the equatorial rim of the capsular bag free from contacts which may exert stress on the capsular bag and which may cause or aggravate inflexibility of the capsular bag.

The lens system may be provided with at least one element for defining a default configuration of at least the two lenses, thus allowing to define and determine optical parameters such as the focal length of the lens system clearly and reproducibly.

Preferably, the focal length of the lens system in the default configuration is such that an eye wherein the lens system is implanted is emmetropic at the default configuration of the lens system. This provides the patient with optimum vision at "infinity". An emmetropic default configuration can also be reliably checked and possibly attained during or after implantation by allowing the ciliary muscle to relax, e.g. by letting the patient focus at an "infinitely" distant object or by a medicinal preparation or procedure, thus obtaining a reference position of the capsular bag.

Yet another aspect of the present invention is an intraocular lens for implantation in the capsular bag of an eye having an optical axis, comprising an optical system and a frame. The frame comprises an anterior frame element, a posterior frame element, and a resilient element for urging the anterior and posterior frame elements towards a predetermined axial separation. The frame further comprises a connecting element connecting the anterior and posterior frame elements. The optical system is attached, in use, to the connecting element and is separate from the anterior and posterior frame elements.

The predetermined axial separation should preferably be chosen such that the anterior and posterior frame elements are urged against the anterior and posterior inner wall, respectively, of the capsular bag when implanted therein.

Thus, the optical system is free from contact with the capsular bag such that both the capsular bag and the optical system may be flushed with aqueous humor inside the capsular bag, thus reducing cell migration and growth and subsequent opacification thereof.

In some embodiments, a kit is provided for the implantation of an intraocular lens in the capsular bag of an eye, comprising a biocompatible material for filling the capsular bag, preferably substantially homogeneously, and replacing the natural lens tissue of the eye, and an intraocular frame. The frame comprises an anterior frame element, a posterior frame element, and a resilient element for urging the anterior and posterior frame elements against the anterior and posterior inner wall, respectively, of the capsular bag when implanted therein, the frame being arranged for biasing the capsular bag towards the accommodating shape.

In this way, a natural lens may be emulated. The effective resiliency and force of the artificial lens towards the accommodating shape may be selected by the material choice for the lens material and the resilient properties of the frame, thus allowing to select an optimum combination of properties for the assembly for implantation and use.

The frame, once implanted in the capsular bag of the eye, is preferably in contact with the interior surface thereof on the anterior and posterior walls thereof and is free from contact with the equatorial rim thereof. Thus the capsular bag is essentially free from stress in the equatorial plane, and the natural force-balance of the eye may be relatively closely matched.

Preferably, at least the posterior frame element is provided with a sharp edge along the contact region of the frame element with the wall of the capsular bag. This obstructs cellular migration from passing within a perimeter set by the sharp edge which may cause cellular growth and subsequent opacification and/or stiffening of the capsular bag within the contact region.

The frame, the lens and/or the optical system may be so configured that particular aspects thereof, such as the forces the different elements exert to each other and/or to the capsular bag or optical parameters such as the focal length of a lens are adjustable prior, during and/or after the implantation thereof. Further, any part may be formed foldable, rollable generally deformable for insertion into the capsular bag with minimal damage.

In one embodiment, accommodating vision may be installed in a patient by implanting an intraocular lens system or an intraocular lens into the capsular bag of the eye after having removed the natural lens tissue therefrom, or by implanting a frame according to an embodiment of the present invention and attaching an optical element thereto.

Additionally, accommodating vision may be installed in a patient following the steps of removing the natural lens tissue of an eye, while leaving the capsular bag essentially intact, and implanting an intraocular frame comprising: an anterior frame element, a posterior frame element, and a resilient element for urging the anterior and posterior frame elements against the anterior and posterior inner wall, respectively, of the capsular bag when implanted therein, the frame being arranged for biasing the capsular bag towards the accommodating shape, and filling the capsular bag with a biocompatible material for replacing the natural lens tissue preferably substantially homogeneously.

The thusly formed artificial lens enables natural-like accommodation. The opening or openings which has (have) to be made during the surgery for the removal of the natural lens and/or the insertion of the device or devices being implanted may be covered or closed with any known technique such as suturing, gluing, covering with a biocompatible material etc.

A suitable optical system for use with an embodiment of the present invention exhibits a varying focal power upon a relative rotation of the lenses. An effective optical system may be realised with two or more appropriately formed varifocal lenses.

In some embodiments, a relatively straightforward method of determining the relevant shape of the lenses or determining relevant parameters therefor has been discovered. The result is a rather simple equation for the optimal shape of the lens profile. An accordingly shaped optical system exhibits a very large focussing range for a relatively small angular displacement. The change in focal length of the system in relation to the rotation may be determined to suit a particular purpose or use.

According to an embodiment of the present invention, two lenses may be formed to contain a profile to form a compound lens system, comprised of two or more individual lenses, with optical power P, wherein the power P is variable dependent on a rotation of both lenses by an angle, e.g. $2\nu$ radians, with respect to each other, e.g. $\nu$ rad in mutually opposite directions with respect to a particular starting configuration, about a single axis which is situated a distance, e.g. $y_0$, from the optical axis of the compound lens and which rotational axis is parallel to the optical axis.

To determine a proper lens shape, consider two lenses extending essentially parallel to each other and perpendicular to an axis z. The thickness profile $\Delta z$, i.e. the variation of the lens thickness in the direction z, as a function of position on the lens, of both lenses may be expressed using a parameter A with the dimension $(mm\, rad)^{-1}$. The parameter A, which is an amplitude of the profile $\Delta z$, determines a linear rate of optical power change with rotation $\nu$.

In cylindrical coordinates $(r,\phi,z)$ the thickness profile $\Delta z$ is given by:

$$\Delta z(r,\phi) = -A\nu\{r^2\cos^2\phi + (r\sin\phi - y_0)^2\}. \tag{1}$$

The thickness profile $\Delta z(r,\phi)$ should preferably be symmetrical about a rotation over $\nu$ radians. Thus the function $z(r,\phi)$ describing the profile of the surface of each lens should obey:

$$\Delta z(r,\phi) = z(r,\phi-\nu) - z(r,\phi+\nu) \tag{2}$$

Eq. (2) may be transformed by taking the Taylor approximation to first order of the thickness profile $\Delta z(r,\phi)$ about $\phi$ for small $\nu$. This yields:

$$z(r,\phi-\nu) - z(r,\phi+\nu) = \Delta z(r,\phi) \approx -2\nu d_\phi\{z(r,\phi)\},$$

wherein $d_\phi\{z(r,\phi)\}$ indicates the partial derivative to $\phi$ of $z(r,\phi)$. Substituting Eqs. (1) and (2) into Eq. and omitting constant terms results in the following differential equation:

$$d_\varphi\{z(r,\varphi)\} = \frac{1}{2}A(r^2\cos^2\varphi + r^2\sin^2\varphi - 2y_0 r\sin\varphi) \tag{4}$$
$$= \frac{1}{2}A(r^2 - 2y_0 r\sin\varphi)$$

Solving the differential equation (4) yields the following, rather simple profile equation $z(r,\phi)$ for the surface profile of each lens:

$$z(r,\phi) = \frac{1}{2}Ar^2\phi + A\, y_0 r \cos\phi + E. \tag{5}$$

wherein E is an integration constant.

Eq. (5) may be extended with terms which superpose the surface profile $z(r,\phi)$ on another profile, but which do not influence the thickness variation $\Delta z(r,\phi)$ with respect to this profile per se:

$$z(r,\phi) = \frac{1}{2}Ar^2\phi + Ay_0 r \cos\phi + Br + Cr^2 + D\phi + E. \tag{6}$$

The parameters B, C, D and E in Eq. (6) may be used to optimise the lens profile, e.g. to minimise the total lens thickness and/or to optimise its optical quality.

The above derivation of Eqs. (5) and (6), respectively, may be extended by including higher order terms of the Taylor expansion of Eq. (2), e.g. to further optimise the lens shape and reduce possible aberrations.

To calculate a suitable value for A, it may be observed that the relation between the power of a parabolic thin lens and the curvature of its surface is generally defined as:

$$P = (n_2 - n_1)/R, \tag{7}$$

wherein P is the power of the lens in dioptre (Dpt), $n_1$, $n_2$ are the indices of refraction of the lens material and the surrounding material, respectively, and R is the radius of curvature of the lens surface in millimeters.

For a lens having a surface given by Eq. (5), the lens power may be chosen to vary with A 2v, as indicated above. Thus the relation between the parameter A and the radius R of an equivalent spherical thin lens is given by:

$$R=(2Av)^{-1}. \qquad (8)$$

Thus the lens power P(v) as a function of the rotation of the lenses is given by:

$$P(v) = P_0 + 2A(n_2 - n_1)v \qquad (9)$$
$$= P_0 + \Delta P(v),$$

wherein $P_0$ is the lens power for a default configuration with $v=v_0$ rad mutual rotation between the lenses. Preferably, $v_0=0$ rad. Conversely, for designing a particular compound lens the value of A may be chosen from:

$$A = \{P(v) - P_0\}/\{2(n_2 - n_1)(v - v_0)\} \qquad (10)$$
$$= \Delta P(v)/\{2(n_2 - n_1)\Delta v\},$$

and substituting appropriate values for the intended purpose of the lens system.

For optical systems wherein the lens power is given by another equation than Eq. (8), the derivation of an expression for P(v) and A may be performed analogously.

The parameter A need not be linear but may in itself also be a function of one or more variables $A(r,\phi,z)$, dependent on the choice of the variation of the lens power P with relative displacement of the lenses $P(r,\phi,z)$.

A convex-convex lens may have outer surfaces with a parabolic shape. For a compound parabolic accommodating lens, the four surfaces are given by the following equations (cf. Eq. (6)):

$$z_3 = \tfrac{1}{2}C_3 r^2 - C_3 y_0 r \sin\phi + E_3. \qquad (11)$$

$$z_4 = \tfrac{1}{2}Ar^2\phi + Ay_0 r \cos\phi + B_4 r + C_4 r^2 + D_4\phi + E_4. \qquad (12)$$

$$z_5 = \tfrac{1}{2}Ar^2\phi + Ay_0 r \cos\phi + B_5 r + C_5 r^2 + D_5\phi + E_5. \qquad (13)$$

$$z_6 = \tfrac{1}{2}C_6 r^2 - C_6 y_0 r \sin\phi + E_6 \qquad (14)$$

wherein the surfaces of the lenses are identified with the numerals 3 (anterior surface of the anterior lens), 4 (posterior surface of the anterior lens), 5 (anterior surface of the posterior lens) and 6 (posterior surface of the posterior lens). $B_4$, $C_4$ and $D_4$ should be equal to $B_5$, $C_5$ and $D_5$, respectively for a cancelling of the thickness variation in a default position, preferably at $v=v_0=0$, and for ensuring a linear and consistent effect of the rotation. The values $E_{1-6}$ represent the positions of the respective surfaces. In the case that $z_4$ and $z_5$ are formed so that their focussing effects cancel at a rotation angle of $v=v_0=0$, $z_3$ and $z_6$ determine the default lens power. $z_3$ and $z_6$ are mainly determined by the values of $C_3$ and $C_6$. For a symmetric lens having a mid-plane at z=0, $z_3$ and $z_6$ are mirror images with $C_3=-C_6$ and $E_3=-E_6$. Preferably $C_3=-C_6=\tfrac{1}{2}R$ (cf. Eqs. (7) and (8)).

Such an optical system may be used for any purpose where an adjustable focal lens shift is desired, inter alia for cameras, telescopes etc. A benefit is that a substantial change in focal length may be achieved by simply rotating one or two lenses in one plane. This requires substantially less energy and space than displacing a lens over appreciable distances along the optical axis of an optical system, as with telescopes known in the art. Further, each rotating lens may be attached to a single common axis, allowing a proper and reliable relative orientation essentially throughout the entire focussing range.

As an example, for calculating a compound lens for use as an intraocular lens in a human eye, the values according to the following Table 1 may be used:

TABLE 1 values for calculating an intraocular accommodating lens.

| | |
|---|---|
| Base refraction at accommodation, $P_0$ | 32 Dpt |
| Refraction at emmetropy, $P_{emm}$ | 24 Dpt |
| Diameter of each lens | 5.5 mm |
| Offset between optical/rotational axes, $y_0$ | 3.5 mm |
| Rotation for accommodation, per lens, $v_{acc}$ | ±0.10 rad = ±5.7° |
| Refractive index of aqueous humor, $n_1$ | 1.336 |
| Refractive index of lens material PMMA, $n_2$ | 1.498 |

Substituting the values of Table 1 in Eq. (10) it can be found that the optical system exhibits the desired accommodation scope $\Delta P(\Delta v=0.10$ rad$)=8$ Dpt for A=0.247.

An optical system with the optimum combination of minimum lens thickness and best optical quality may be obtained by inserting the values for A and for $y_0$ into Eqs. (11)-(14), taking $C_3=-C_6=\tfrac{1}{2}R$, and optimising the other parameters, which may be done numerically.

A suitable result is summarized in the following Table 2:

TABLE 2 overview of suitable parameters for an accommodating intraocular lens according to an aspect of the present invention.

| | |
|---|---|
| $Y_0$ | 3.5 mm |
| A | 0.247/mm rad |
| $B_4 = B_5$ | 0 |
| $C_3 = -C_6$ | 0.0988/mm |
| $C_4 = C_5$ | −0.1940 mm |
| $D_4 = D_5$ | 1.0142 mm/rad |
| $E_3 = -E_6$ | −0.25 mm |
| $E_4$ | −1.82 mm |
| $E_5$ | −1.35 mm |

The surfaces $z_3$ and $z_6$ may also be shaped to provide a non-rotationally symmetric compound lens, e.g. for the correction of astigmatism, to reduce spherical aberration of the compound lens and/or improve off-axis optical performance of an accommodative intraocular lens.

The thickness profile $\Delta z(r,\phi)$ of an aspheric lens may be described by the following conic of revolution:

$$\Delta z(r,\phi) = -cr^2/\{1+(1-k c^2 r^2)^{1/2}\}, \qquad (15)$$

wherein c represents the curvature of an equivalent thin lens. The asphericity of the surface is expressed by the conic constant k which indicates the change in gradient of the surface (k<1: reducing gradient, flattening; k>1 increasing gradient, becoming steeper) with distance from the apex. k thus indicates the degree to which an aspheric thin lens differs from the equivalent spherical form. Depending on the value of k, the lens surface is a hyperboloid for k<0, a paraboloid for k=0, a prolate ellipsoid for 0<k<1, a sphere for k=1, and an oblate spheroid for k>1.

Using a Taylor approximation to the fourth order of Eq. (15) the following expression is obtained:

$$\Delta z(r,\phi) = -\tfrac{1}{2}cr^2 - k/8 c^3 r^4. \qquad (16)$$

Eq. (16) and the differential equation Eq. (4) may be combined as indicated above.

Using a thickness profile with variable power according to c=2 A v and a conic constant k the following relatively straightforward analytical expression, which contains the parameters A, $y_0$ and k, is obtained for the profile $z(r,\phi)$:

$$z(r, \varphi) = \frac{1}{2}Ar^2\varphi + Ary_0\cos\varphi + \frac{1}{2}A^3k\varphi r^4 + 2A^3k\varphi r^2 y_0^2 + \frac{1}{2}A^3k\varphi y_0^4 + \qquad (17)$$
$$2A^3kr^3y_0\cos\varphi + 2A^3kry_0^3\cos\varphi - \frac{1}{2}A^3kr^2y_0^2\sin 2\varphi + E.$$

It should be noted that the effective asphericity of the compound lens is dependent on the amount of rotation v.

The surface profile in (17) may be extended with higher order terms for minimising thickness and optimising optical quality of the individual lenses and the compound lens.

The embodiments of present invention will hereafter be explained in more detail with reference to the figures.

BRIEF DESCRIPTION OF THE FIGURES

FIGS. 1A and 1B show a schematic cross-section of a frame and its operation according to an aspect of the present invention implanted into the capsular bag of a human eye in both in accommodated and in desaccommodated state.

FIGS. 2A and 2B show a schematic cross-section of the frame implanted into a capsular bag according to FIGS. 1A, 1B wherein the capsular bag is provided with a plug to close a rhexis.

FIG. 3 shows a schematic cross-section of the frame implanted into a capsular bag according to FIGS. 1A, 1B, wherein the capsular bag is provided with a window to close a rhexis.

FIG. 4 shows a schematic cross-section of the frame implanted into a capsular bag provided with a window according to FIG. 3, wherein the window is provided with an additional lens.

FIGS. 6A and 6B show a schematic cross-section of a deformable intraocular lens system attached to a frame and implanted into a capsular bag according to FIGS. 1A, 1B.

FIG. 7 shows a perspective side view of an embodiment of an intraocular lens according to the present invention.

FIG. 8 shows a front view along the optical axis of the embodiment of FIG. 7.

DETAILED DESCRIPTION

Figure 5A:
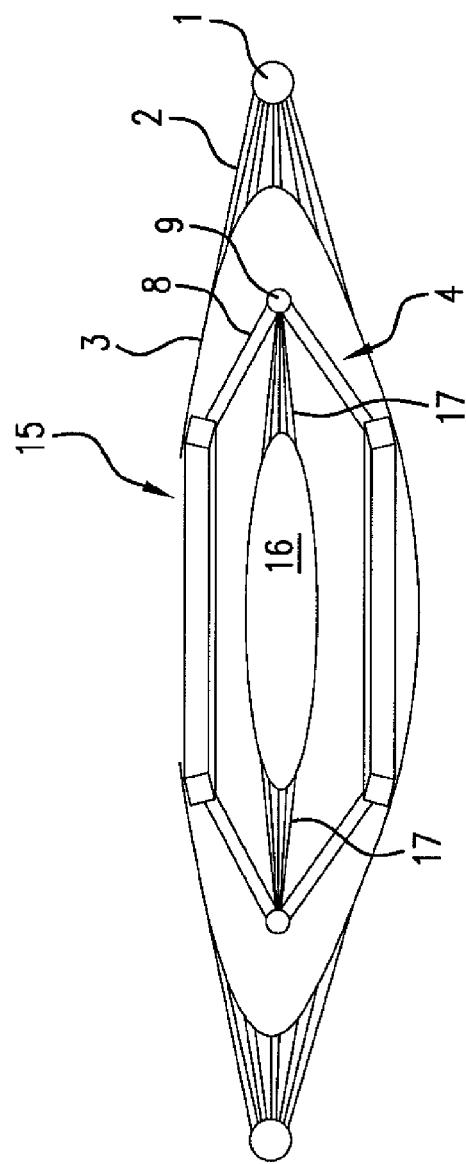
FIGS. 5A and 5B show a schematic cross-section of a deformable intraocular lens attached to a frame and implanted into a capsular bag according to FIGS. 1A, 1B.

FIGS. 1A-6B show a schematic cross-section of a part of a human eye, which is substantially rotationally symmetric about the optical axis OA. The top side of the figures is the front or anterior side of the eye (marked "Ant." in FIGS. 1A, 1B), the bottom side is the rear or posterior side (marked "Post." in FIGS. 1A, 1B).

FIGS. 1A-6B show the ciliary muscle 1, the zonulae 2 and the capsular bag 3. A frame 4 is implanted in the capsular bag 3. The zonulae 2 are attached to the ciliary muscle 1 and the capsular bag 3 and connect these.

The zonulae 2 are attached to the capsular bag 3 around its equatorial rim, which extends along the surface of the capsular bag for approximately 2.5 mm anterior and posterior of the equatorial plane of the capsular bag 3 with respect to the optical axis OA. The equatorial plane is spanned by the line of maximum girth of the capsular bag 3 and the ciliary muscle 1.

The frame 4 as shown comprises an anterior frame element 5, a posterior frame element 6, two resilient elements 7, and two connecting elements 8 which connect the anterior and posterior frame elements 5, 6. The anterior and posterior parts of the connecting elements 8 are movable with respect to each other, in FIGS. 1A-1B schematically indicated with rotational or flexible joints 9.

In certain embodiments, once implanted, the frame 4 is in contact only with the anterior and posterior walls of the interior surface of the capsular bag 4, and is free from contact with the equatorial rim of the capsular bag. In such embodiments, the capsular bag may be essentially free from stress in the equatorial plane, and the natural force-balance of the eye may be relatively closely matched. Accordingly, the overall diameter of the frame 4 in a direction perpendicular to the optical axis OA and/or the diameter of each frame elements 5, 6 are selected to provide this limited contact area within the capsular bag 4. In such embodiments, the outer diameter of each frame element 5, 6 may be between about 5 mm and about 8 mm, or between 5.5 mm and 7.0 mm. Alternatively or additionally, the overall maximum diameter of the frame 4 (e.g., between the flexible joints 9 in the illustrated embodiment) may be less than 10 mm, less than 9 mm, or even less than 8 mm or 8.5 mm. In some embodiments, contact with the anterior and posterior walls only of the capsular bag 4 is provided by selection of the spacing along the optical axis OA between the outer portions of the frame elements 5, 6 (e.g., the portions of the frame elements that contact the capsular bag 4). For example, the spacing along the optical axis OA between the outer portions of the frame elements 5, 6 when the frame 4 is in an unstressed state may be selected to be at least 4 mm, 5 mm, or 6 mm, the selection being influenced at least in part by the size of the capsular bag and whether the unstressed state of the frame 4 is intended to provide an accommodated state or a disaccommodated state after implantation.

The connecting elements 8 may be integrated with the resilient elements 7, as shown in the embodiments shown in FIGS. 2-13. In the shown embodiments the upper and lower arms of the connecting elements 8 deflect away from one another along the optical axis OA.

When the ciliary muscle 1 is relaxed, the zonulae 2 are stretched taut and pull on the capsular bag 3, as shown in FIG. 1A. When the ciliary muscle 1 is tensioned, it contracts so that its diameter reduces and the capsular bag 3 may expand along the optical axis OA, as shown in FIG. 1B.

In a natural eye the resiliency of the lens is essentially provided by the lens tissue. Upon removal of the lens tissue this resiliency is substantially lost. This loss may be at least partially compensated by the resiliency of the frame 4.

The resilient elements 7 urge the anterior and posterior frame elements 5, 6 against the anterior and posterior wall portions of the capsular bag 3 with sufficient force to bias the capsular bag 3 to an accommodating shape upon contraction of the ciliary muscle 1. However, the force produced by the resilient element 7 is sufficiently weak such that the capsular bag 3 and the frame 4 can be flattened upon relaxation of the ciliary muscle 1 (as seen in FIG. 1A).

The resilient elements 7 may be formed of any kind of resilient material, including massive rods or hollow tubes, or plastic or metallic springs. For implantation in an eye the elements should be formed biocompatible, e.g. by the material properties themselves or by being coated with a biocompatible material etc. The other parts of the frame may be formed analogously.

In some embodiments the function of the resilient elements 7 is incorporated into the connecting elements 8. In such embodiments a separate resilient element 7 may be eliminated.

The edges of the anterior and posterior frame elements 5, 6 are provided with a sharp edge along the rim forming the contact region of the frame element 5, 6 with the inner wall of the capsular bag 3, serving to obstruct cellular migration across the inner wall of the capsular bag 3 into the interior of the rim of the frame elements 5, 6.

In operation, tension in the zonulae 2 relaxes upon a contraction of the ciliary muscle 1 and the frame 4 biases the capsular bag 3 to the accommodating shape, as indicated with arrows in FIG. 1B. Thus, the anterior and posterior frame elements 5, 6 undergo a first displacement in a direction substantially along the optical axis OA. This causes a second displacement of the connecting elements 8 in the form of a stretching, whereby the joints 9 are displaced substantially perpendicular to the optical axis OA, as indicated with arrows in FIG. 1B. The displacements of different points along the connecting elements 8 comprise different contributions along and perpendicular to the optical axis OA. The actual displacement of each point depends on the actual shape and possible resiliency of the connecting elements 9. As used herein, the term "substantially", when used to indicate approximate angular orientation (e.g., "substantially parallel", "substantially along", "substantially perpendicular", and the like) mean to within plus or minus 10 degrees.

The natural human eye lens is asymmetrical; the anterior half is flatter than the posterior half with respect to the equatorial plane. Correspondingly, the joints 9 may be positioned offset from the middle of the connecting elements 8, or the resiliency of a resilient element 7 may vary along its length.

In order to implant a frame 4 into the capsular bag 3 of an eye, the capsular bag 3 has to be opened to form an opening 11. This opening 11, also called rhexis, should be sufficiently large so that the frame 4 may be inserted into the capsular bag 3, yet be as small as possible to avoid complications such as ruptures, scarring etc.

FIGS. 1, 2 and 3 show that the rhexis 11 may be closed by in any suitable way known in the art such as suturing or gluing (FIG. 1) by an artificial plug 12 (FIG. 2; plug not drawn to scale) or by a, preferably flexible, window 13 (FIG. 3).

The closure of the rhexis 11 may serve to assist maintaining integrity of the capsular bag 3 and/or to maintain the contents of the capsular bag 3 therein. These contents may be aqueous humor, an artificial biocompatible lens material emulating natural lens tissue or even the natural lens tissue. The effective resiliency of the frame 4, which may be expressed as a spring constant $C_s$, may be configured to equal that of a healthy, young natural lens.

In case the refraction of the contents is insufficient for proper accommodation, the window 13 may be integrated with a lens 14, as shown in the particular embodiment of FIG. 4.

It is, however, preferred that the rhexis 11 be left open at least partially to allow the exchange of aqueous humor between the anterior chamber of the eye and the inside of the capsular bag 3. E.g. the plug 12 of FIG. 2 may be designed to allow aqueous humor to pass but to maintain a less-fluid implanted lens material inside the capsular bag 3. Further, an open rhexis allows to equate the interior pressure of the anterior chamber and the capsular bag during accommodation and desaccommodation.

In the art it is known to excise a window from the anterior wall of the capsular bag 3, in order to allow an essentially unobstructed flow of aqueous humor through the capsular bag 3 which is thought to help prevent cell growth and scarring of the wall of the capsular bag 3, as discussed supra. When using a frame 4, the reversible deformation of the capsular bag 3 by the action of the ciliary muscle is maintained, causing the aqueous humor to flow and be exchanged due to a pumping effect.

The tissue forming the rim of the rhexis, especially in case of one with a rather large diameter, may become rather flabby which may influence the behaviour of the capsular bag. This may be prevented to a relatively large extent by attaching the rim of the rhexis 11 to the anterior frame element by any suitable technique, such as gluing, suturing, stapling, clamping or clasping etc. An additional element or ring outside the capsular bag may be provided for this purpose. Similarly, a rhexis window 13, 14 may be attached to the frame, both with and without also affixing the capsular bag tissue at the same time.

FIG. 5 shows an embodiment of an intraocular lens (hereinafter also referred to as "IOL") 15, comprising a frame 4 and a reversibly deformable lens 16. The lens 16 is attached to the joints 9 of at least two connecting elements 8 of the frame 4 by means of one or more artificial zonulae 17. The lens 16 is resilient and preferably has a relaxed shape which is strongly curved or essentially spherical, similar to that of a natural lens. It is equally conceivable to realise the lens 16 as a bag containing a reversibly deformable material such as a material of a resilient, visco-elastic, fluid or even gaseous nature. The connecting elements 8 may be resilient or not. In this latter configuration the resilient properties of the IOL 15 as a whole may be derived from the resiliency of the lens 16.

Figure 5B:
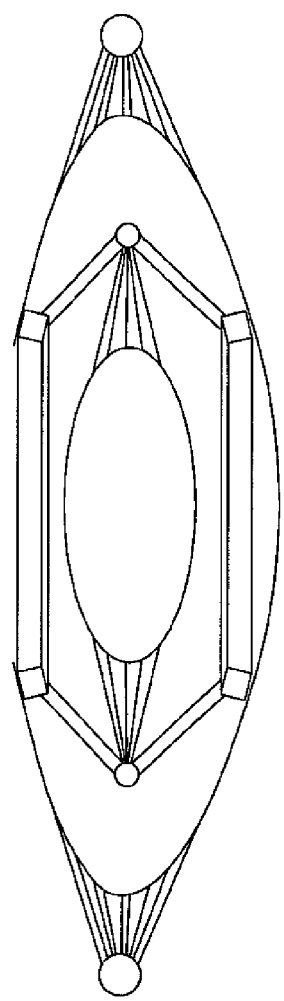

In operation the action of the ciliary muscle 1 on the capsular bag 3 is transmitted to the IOL 15, and via the frame 4 thereof to the lens 16. Conversely, the forces caused by the resiliency of the lens 16 and/or other elements of the IOL 15 are conveyed to the capsular bag and urge it towards accommodation (FIG. 5B). Thus, an accommodating IOL is provided which emulates the operation of a natural lens. The lens 16 is free from contact with a wall of the capsular bag 3, so that all surfaces may be rinsed by the aqueous humor.

FIGS. 6A and 6B show a schematic view of an embodiment of an IOL 15 provided with an reversibly deformable compound lens 18 attached to a frame 4. The lens 18 is an optical system 18 comprising two optical elements, in the form of two varifocal lenses 19, 20 which are movable with respect to each other.

In operation the action of the ciliary muscle 1 on the capsular bag 3 is transmitted to the IOL 15, and via the frame 4 thereof to the optical system 18, such that the lenses 19 and 20 are displaced with respect to each other. In the shown embodiment, the lenses 19, 20 substantially fully overlap in the accommodating position FIG. 6B and are displaced with respect to each other when the ciliary muscle 1 is relaxed (FIG. 6A). The opposite situation of overlapping lenses 19, 20 for a relaxed ciliary muscle 1 and displaced lenses for accommodation, or any other overlapping or non-overlapping arrangement may be constructed equivalently.

In the shown embodiment, the centres of both lenses 19, 20 are symmetrically offset from the optical axis for a relaxed ciliary muscle (FIG. 6A). Asymmetric displacement is also possible, e.g. by mounting only one lens movable to a connecting element 8 of the frame 4, by attaching both lenses to the same connecting element 8 or to parts of connecting element 8 exhibiting different displacement paths.

The lenses 19, 20 may be formed according to Eqs. (11)-(14) with the parameters of Tables 1 and 2, but other shapes or other optical objects are also possible.

FIGS. 7 and 8 show a side view and a front view, i.e. seen on the anterior side, of a preferred embodiment of an IOL 21. The operation of the IOL is according to the principle indicated in FIG. 6.

The IOL 21 comprises a frame 22 and an optical system 23. The frame 22 comprises an anterior frame element 24, a posterior frame element 25, first and second resilient connecting elements 26A, 26B to each of which haptics 27, 28 are attached. The first and second resilient connecting elements 26A, 26B deflect radially outward, relative to a straight connection between the anterior and posterior frame elements 24, 25, by being bent.

The optical system 23 comprises a compound lens 29 in turn comprising two varifocal lenses 29A, 29B. The lenses 29A, 29B are each attached to the first or second connecting element 26A, 26B, by means of a connecting arm 30A, 30B, respectively.

The arms 30A, 30B are attached to the resilient connecting elements 26A, 26B at the position of their maximum outward deflection. The arms 30A, 30B extend essentially radially with respect to the symmetry axis of the lens 29 and the frame 22 and are formed flexible and/or resilient.

The optical system 23 further comprises an interconnection 31 for mutually movably interconnecting the lenses 29A, 29B. The interconnection 31 comprises arms 32A, 32B which are connected to each lens 29A, 29B, respectively, and which are joined at joint 33.

The interconnection 31 provides additional stability to the relative position of the lenses 29A, 29B, inter alia to prevent the lenses from touching each other. The interconnection 31 further provides a centre of rotation, at the joint 33, for the rotation of the individual optical elements 29A, 29B with respect to each other. The axis of rotation is substantially parallel to the optical axis of the optical system 23.

The joint 33 may be formed in any suitable manner, e.g. be the result of the entire optical system 23 or the entire IOL 21 being a monolithic object. The joint may also be formed as a glued or welded connection or be a hinge etc. In the embodiment shown in FIGS. 7, 8, the interconnection 31, and thus the joint 33, is formed as a monolithic element, attached to the lenses 29A, 29B.

Here, the interconnection 31 also forms a resilient element for providing a restoring force for urging the elements of the optical system 23 to a default configuration. The default position of the IOL 21 as a whole, in the absence of external forces, depends on the interaction of all its elements under the influence of the different resilient elements 26A, 26B, 31. In the shown embodiment the lenses 29A, 29B are substantially overlapping (FIGS. 7, 8). In this position the compound lens 29 preferably has a lens power of approximately 32 Dpt, for providing a focal length for nearby vision.

Preferably, the IOL 21 is arranged or implanted such that the symmetry axis of the frame and the optical axis of the optical system 23 coincide with the optical axis of the eye, and the points or regions of bending or flexing of the connecting elements 26A, 26B lie in the equatorial plane of the capsular bag. The connecting elements 26A, 26B are thus asymmetric with respect to the equatorial plane.

To account on the one hand for the asymmetry of the capsular bag of a human eye with respect to the equatorial plane and on the other hand for the desired symmetry of the relative displacement of the lenses 29A, 29B, the posterior sections of the resilient connecting elements 26A, 26B, are provided with reinforcements 34A, 34B, respectively. The reinforcements 34A, 34B counteract the fact that in this embodiment the posterior sections of the resilient elements 26A, 26B are longer than the anterior sections thereof, which would naturally lead to a relatively weaker spring force of the posterior section.

The haptics 27, 28 are provided for further assisting the positioning of the IOL 21 into the capsular bag of an eye, relative to the equatorial plane and the optical axis of both the eye and the IOL 21, and for assisting the maintenance of that position after implantation. The haptics 27, 28 are arranged for gently pressing against the equatorial rim of the capsular bag, preferably just sufficiently strong to maintain the position of the IOL 21, but weak enough not to tension or stretch the capsular bag.

The resiliency, shape and/or structural strength of each element of the IOL 21, including the lenses 29A, 29B, may be adaptable, e.g., by removal of material to locally disassemble parts or to weaken or lighten the structure, if so desired. Thus, the forces acting on the capsular bag may be tuned.

Figure 9:
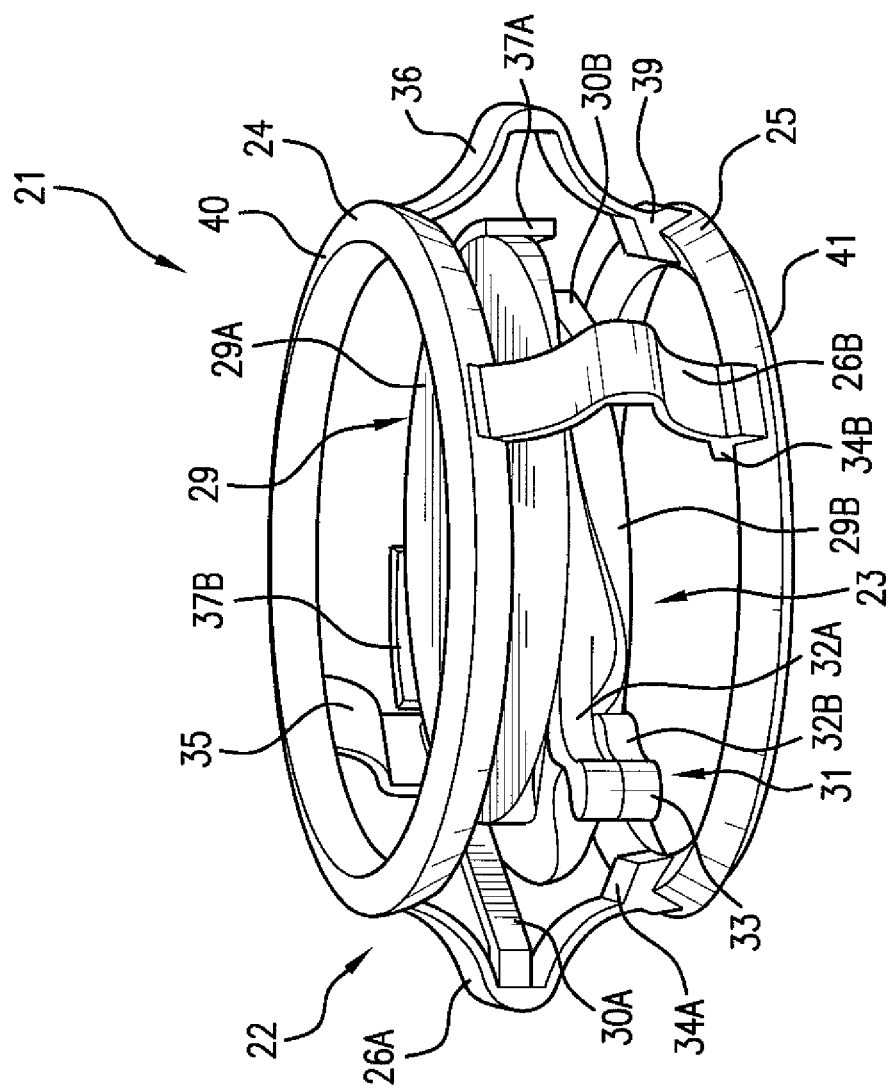
FIG. 9 shows a perspective side view of another embodiment of an intraocular lens according to the present invention.
Figure 10:
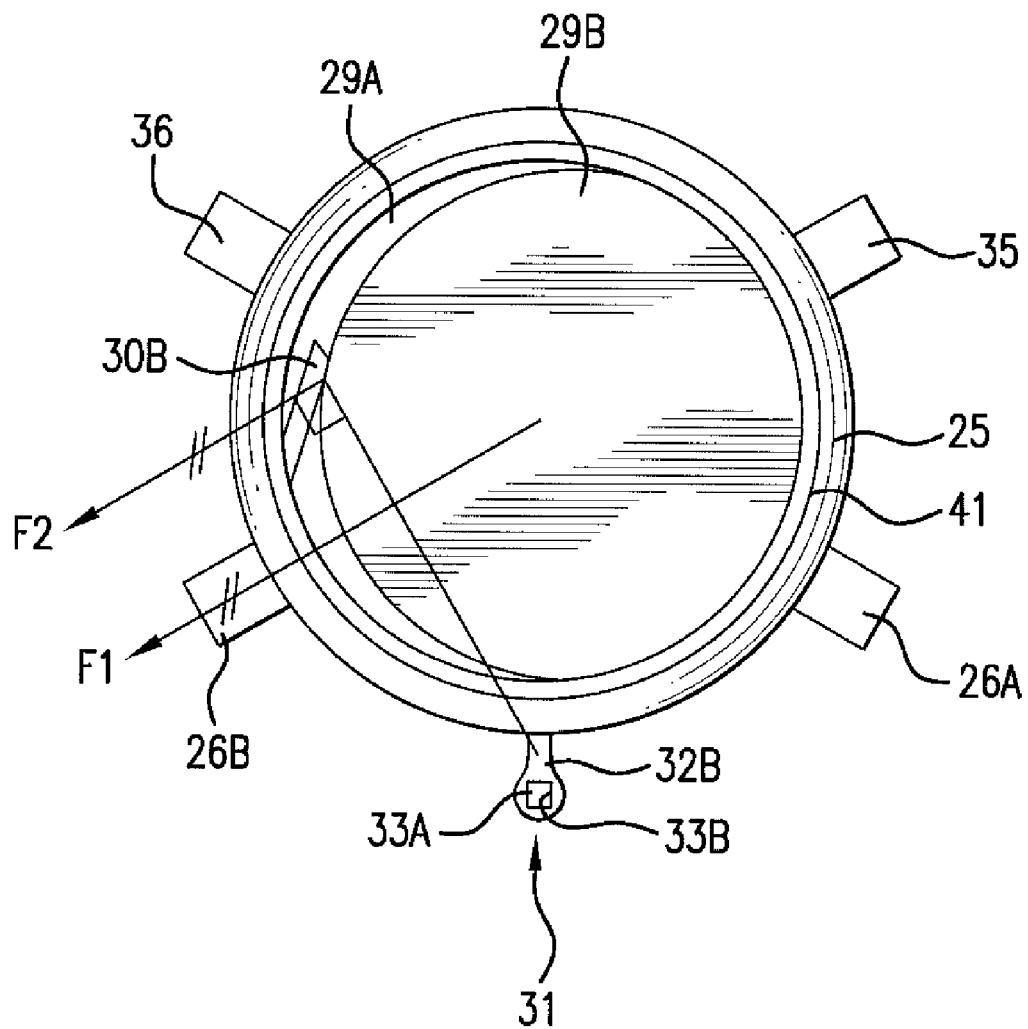
FIG. 10 shows a rear view of the intraocular lens of FIG. 9.
Figure 11:
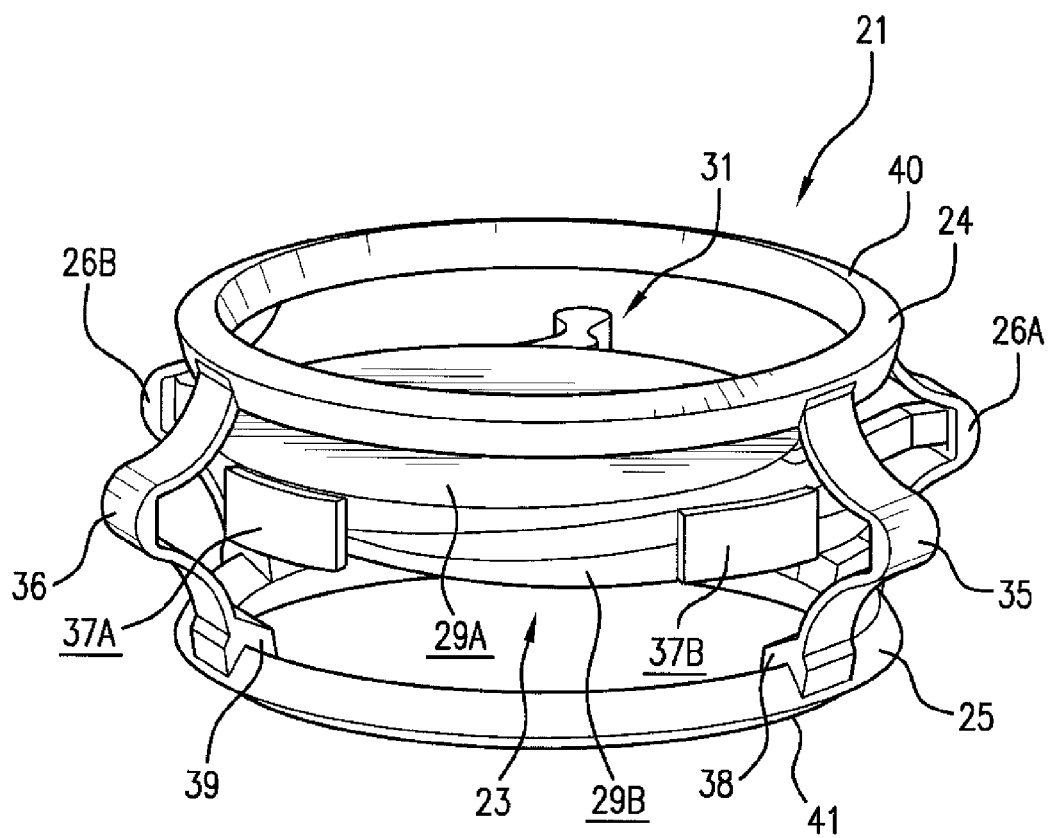
FIG. 11 shows a perspective side view from another angle of the intraocular lens of FIG. 9.
Figure 12:
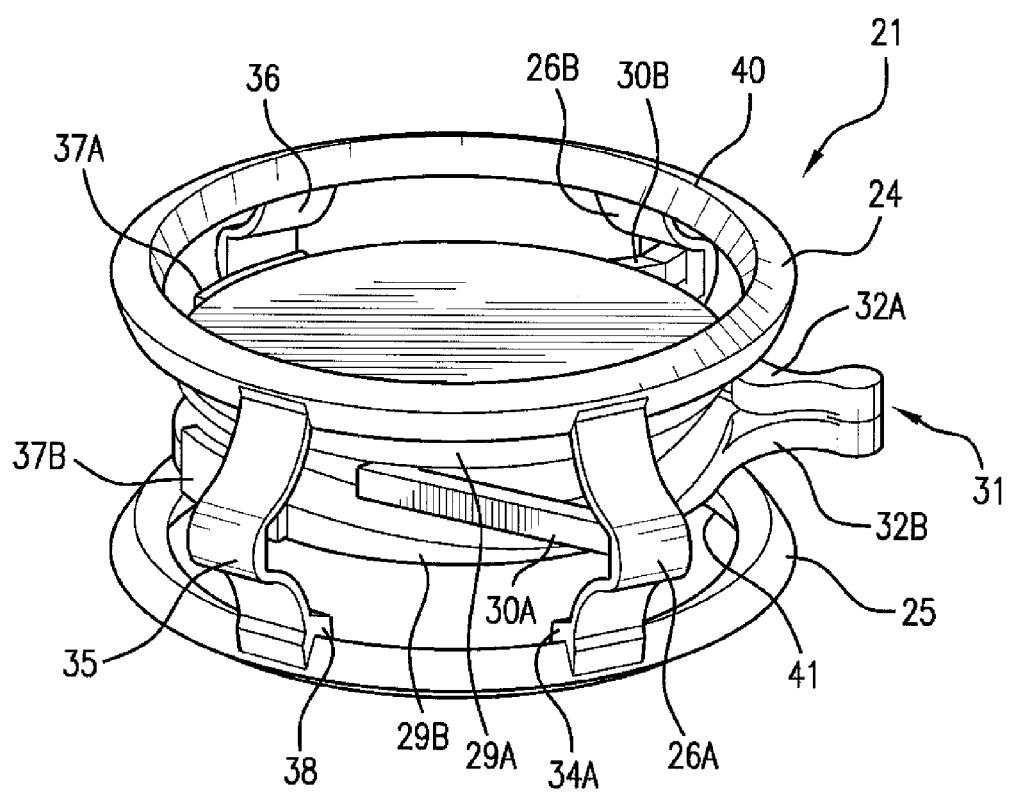
FIG. 12 shows a perspective side view from yet another angle of the intraocular lens of FIG. 9.

FIGS. 9, 11 and 12 show different side views of a second preferred embodiment of an IOL 21. FIG. 10 shows a rear view of this embodiment, i.e. the IOL 21 is shown from the posterior side. In FIGS. 7, 8 and 9-12 substantially equivalent elements are indicated with the same reference numerals.

The first and second connecting elements 26A, 26B of the frame 22 are resilient. The four resilient elements 26A, 26B, 35, 36 are configured for urging the anterior and posterior frame elements 24, 25 against the anterior and posterior inner wall, respectively, of the capsular bag of an eye when implanted therein.

The resiliency of the individual resilient elements 26A, 26B, 35, 36 and the interconnection 31 is preferably chosen or adapted to result in a substantially axial symmetric spring force on the anterior and posterior frame elements 24, 25 upon compression thereof, and thus on the anterior and posterior walls of the capsular bag of an eye when the IOL 21 is implanted therein. Preferably, the IOL 21 is arranged or implanted such that the symmetry axis of the force coincides with the optical axis of the eye, and the points or regions of bending or flexing of the resilient elements 26A, 26B, 35, 36 lie all in the equatorial plane of the capsular bag.

These aspects may be designed and/or adjusted by the dimensions of the parts of the IOL 21, e.g. with the reinforcements 34A, 34B, 38, 39 on the resilient elements 26A, 26B, 35, 36.

The interior edge of the anterior and posterior frame elements 24, 25 are formed as sharp rims 40, 41 for urging into the wall of the capsular bag, to obstruct cellular migration thereunder.

In the second embodiment of FIGS. 9-12, the frame 22 comprises two resilient connecting elements 26A, 26B, to which the optical system 23 is attached, and two additional resilient elements 34, 35, which are only attached to the anterior and posterior frame elements 24, 25 and to which the optical system 23 is not attached. This embodiment does not comprise haptics. Each lens 29A, 29B of this embodiment is further provided with a stop 37A, 37B, respectively, the function of which will be explained below.

In the shown embodiment, the joint 33 of the interconnection 31 between the lenses 29A, 29B is formed by a fitting connection between the arms 32A, 32B by a peg 33A of essentially square cross-section in a matching hole 33B.

The arms 30A, 30B are attached to the connecting elements 26A, 26B in a similar peg-in-hole fashion with a tight fit. This interconnection may be glued, welded or affixed in any suitable manner if necessary. Thus, the IOL is formed as a kit of parts for facilitating fabrication and implantation of the separate components, viz. the frame, the anterior lens and the posterior lens. However, the IOL may be formed and implanted in more or less separate parts or as a single monolithic object.

The interconnection 31 forms a resilient element for providing a restoring force for urging each lens 29A, 29B away from each other. Thus, in this second embodiment the lenses 29A, 29B are rotated with respect to each other in the default configuration of absence of external forces, which is shown in FIGS. 9-12. In this default position the compound lens 29 has a short focal length (high focal power) for nearby vision.

In this embodiment, the arms 30A, 30B which connect the optical system 23 to the frame 22 are fixated resilient and are arranged non-radially.

The arms 30A, 30B are attached to the lenses 29A, 29B such that the essential radial pulling force F1 (see FIG. 10) of the connecting elements 26A, 26B on the arms 30A, 30B causes, in combination with the effective axis of rotation of the interconnection 31, an effective displacement force F2 on the lenses 29A, 29B (see FIG. 10) which is essentially parallel to this radial pulling force F1. The force F2 thus has components both radial and tangential to the axis of symmetry of the frame and/or the entire IOL. As a consequence of this arrangement a variation in the deflection of the connecting elements 26A, 26B is mapped to a relative displacement of the lenses 29A, 29B. The arrangement is preferably such that the mapping is unitarily, i.e. the displacement of the apex of the connecting elements 26A, 26B is equal to that of the lenses 29A, 29B. This facilitates calculating and optimising the behaviour of the IOL.

A further effect of such an arrangement is that the optical axis of the compound lens 29 may remain essentially immobile with respect to the frame upon a rotation of the lenses 29A, 29B.

When implanted in the capsular bag of an eye, a relative displacement of the anterior and posterior frame elements 24, 25 towards each other causes a pulling on the lenses 29A, 29B along the arrow F2, resulting in the lenses 29A, 29B the to be displaced towards an overlapping configuration. Further displacement beyond overlapping is arrested by the lenses 29A, 29B engaging the stops 37B, 37A on the other lens 29B, 29A, respectively. Thus a default configuration is determined.

The arrangement of the arms 30A, 30B also allows a decoupling of the frame 22 and the optical system 23 in the following sense: when the optical system 23 is urged in the default configuration with the lenses 29A, 29B engaging the stops 37B, 37A, further approaching of the anterior and posterior frame elements 24, 25 is enabled since a resulting displacement of the connecting elements 26A, 26B is absorbed by the resilient deformation of the arms 30A, 30B.

Thus, the overlapping default configuration of the compound lens 29 may be achieved and maintained, whereas the frame 22 may still absorb a force by the capsular bag. This second default configuration may be realised when the IOL 21 is implanted in the capsular bag 3 of an eye wherein the ciliary muscle 1 is fully relaxed.

In this second default configuration, which is essentially defined by the combination of the IOL 21 and the eye of the patient, the focal power of the lens 29 is preferably such that the eye is emmetropic. Since the details of each human eye are different, the IOL 21 may be adjustable to achieve this. Adjustments may be made by exchanging or reshaping (one of) the lenses 29A, 29B.

Further, the force balance of the IOL 21 may be adjusted, e.g. by locally removing or ablating material from the interconnection 31, the arms 30A, 30B, the connecting elements 26A, 26B and/or the resilient elements 35, 36. An IOL 21 which is implanted in an eye is considered optimally tuned when the effective forces on the lenses 29A, 29B are set such that with a fully relaxed ciliary muscle the lenses 29A, 29B are just pulled free from the stops 37B, 37A.

The distance for proper focussing at nearby objects (full accommodation), e.g. for reading fine print or for detecting splinters in the skin, may generally be established at 10 cm from the eye. This corresponds to an effective focal power of the lens of at full accommodation of $P_{acc} \approx P_0 \approx 32$ Dpt. Emmetropy is generally achieved for $P_{emm} \approx 24$ Dpt. The optical system may be designed, set to or adjusted to default configurations according to these values.

Preferably, the diameter of the optical system or of the lens, whether or not a compound lens, is chosen such that the edges thereof are shielded by the iris such that distorted vision and aberrations such as coma and glare, e.g. from oncoming traffic, are minimised. A suitable lens diameter for an average human adult is approximately 5.5 mm. A suitable distance between the optical axis of such a lens and the centre of rotation in the case of the IOL 21 of FIGS. 6-12 is 3.5 mm. These sizes may of course be adapted to suit the individual to be treated.

For use in providing accommodating, the IOL preferably is able to provide a change in optical power of at least about 0.25 Diopter per degree of relative rotation between the lenses 29A, 29B, more preferably a change in optical power of at least 0.5 Diopter, 1 Diopter, or even 1.5 Diopters per degree of relative rotation between the lenses 29A, 29B The IOL 21 may also be sized such that the interconnection 31 or other elements accessible from the outside by optical means such as a laser through the pupil when the iris has its maximum diameter. This allows the IOL 21 to be adjusted.

The different configurations of the connecting arms 30A, 30B also at least partially determine the actual path of the displacement of the lenses 29A, 29B, and therewith a possible displacement of the effective optical axis of the compound lens 29, as discussed above for the embodiment of FIGS. 9-12. E.g., for the IOL 21 according to FIGS. 7, 8, and according to Eqs. 11-14 with the values of Tables 1 and 2, the deformation of the optical system 23 for a relative rotation of the lenses 29A, 29B of 0.10 rad, causes the rotational axis through the joint 33 to move towards the symmetry axis of the frame 22. This causes an effective displacement of the optical axis of the compound lens 29 of just under 40 micron. This is considered acceptable for human use.

Due to the fact that the arrangement of the arms 30A, 30B of the embodiment of an equivalent IOL 21 according to FIGS. 9-12 also cause a displacement with a tangential component, the displacement of the optical axis between 0 and 0.10 rad rotation is below 10 micron, which is not noticeable for most patients.

The distance between the rotational axis through joint 33 and the optical axis of the compound lenses 29A, 29B (e.g., $y_0$) is preferably less than the radius of the capsular bag on a typical human subject, for example, less than about 6 mm, preferably less than 5 mm or less than 4 mm. In some embodiments, this distance is even smaller, for example, within the radius of periphery of the lenses 29A and/or 29B (e.g., less than 3 mm or less than 2 mm). Furthermore, the overall size of the IOL 21 is preferably configured to fit entirely within the capsular bag of an eye of a subject. In the case of a human subject, for example, an IOL according to an embodiment of the present invention has a maximum extent in a direction normal to the optical axis thereof that is less than about 15 mm, preferably less than 12 mm, 11 mm, or 10 mm, depending on specific construction of the IOL and the desired accommodative performance.

Figure 13:
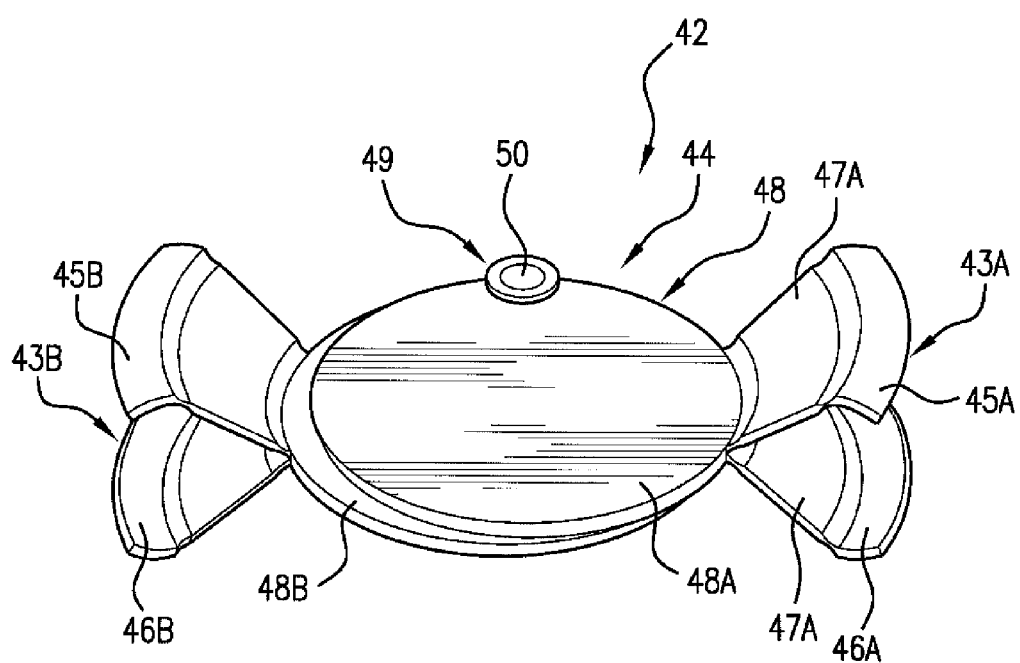
FIG. 13 shows yet another embodiment of an intraocular lens according to the present invention.

FIG. 13 shows a third embodiment of an intraocular lens, which is significantly simpler in construction than the previous embodiments.

The IOL 42 comprises a frame 43 and an optical system 44. The frame 43 comprises two frames halves 43A and 43B, respectively. Each frame half 43A, 43B comprises an anterior frame element 45A, 45B, respectively, and a posterior frame element 46A, 46B, respectively, which are connected by resilient connecting elements 47A, 47B, respectively. The frame halves 43A, 43B may be interconnected by additional elements, e.g. forming a ring or a differently shaped closed rim as in the embodiments discussed before.

The optical system 44 comprises a compound lens 48, comprising varifocal lenses 48A and 48B, respectively. The lenses 48A, 48B are mutually movable connected through interconnection 49. The joint 50 of the interconnection 49 is shaped as a rotatable hinge 50 but may be of any suitable construction.

The resilient connecting elements 47A, 47B of the frame 43 are veered towards the optical axes of the eye and the compound lens 48, respectively. The elements 47A, 47B are connected directly to the lenses 48A, 48B, respectively, at the point of their maximum deflection from a straight connection. In FIG. 13 the connection is relatively broad, but a narrower connection or multiple connections at several positions are also conceivable. Further, a movable connection such as a hinge or a flexible joint may be applied for allowing relative rotations between a frame half 43A, 43B and a lens 48A, 48B.

When implanted into the capsular bag of an eye, the reshaping of the capsular bag as a result of the action of the ciliary muscle may compress the frame 43 substantially parallel to the optical axis of the eye. This, opposite to the previously discussed embodiments causes the lenses 48A, 48B to be pressed, rather than pulled, towards another.

In the embodiment of FIG. 13 The lenses may be provided with stops for determining a default configuration of the optical system for emmetropy. Yet, in the embodiment shown in FIG. 13 with separate frame halves 43A, 43B, the default configuration may be adjusted by simply repositioning the frames halves with respect to each other inside the capsular bag. Preferably, after such adjustment the frame halves 43A, 43B are attached or affixed to the capsular bag and/or to each other for additional stability, security of the position and/or reproducibility of the relative motion and thus of the optical properties of the IOL 42.

The IOL 42 may also be provided as a kit of separate parts to be assembled prior or during operation, similar to the embodiments discussed above.

A frame 4, 22 and/or an IOL 15, 21, 42 or any element thereof may be formed from one or more flexible or resilient materials so that it may be compressed, folded or rolled to a shape with a smaller cross-section than its natural shape. Thus the object may be inserted in the capsular bag 3 through a relatively small rhexis. The material may also be a somewhat gelatinous substance which sets to a firmer material under reaction with the aqueous humor, when exposed to body temperature or when irradiated with an appropriate wavelength, such as infrared or ultraviolet radiation, etc. Such radiation may be delivered by laser, which also allows to provide local variations in the properties of the material. Laser irradiation may also be used to weld or even ablate material so as to assemble or adjust optical or generally structural elements and/or properties thereof. A frame 4 and/or an IOL 15, 21, 42 and/or elements thereof may be provided implantation-ready or as a kit of parts to be assembled. Such, and different, materials and procedures which may be performed prior, during or after insertion into an eye are generally known in the art.

In the shown embodiments the anterior and posterior frame elements 5, 6; 24, 25 are annularly shaped, but may have any desired shape. It is, however, preferred that they are symmetrical, to provide a homogenous force distribution on the capsular bag and to prevent it from damage.

Figure 14:
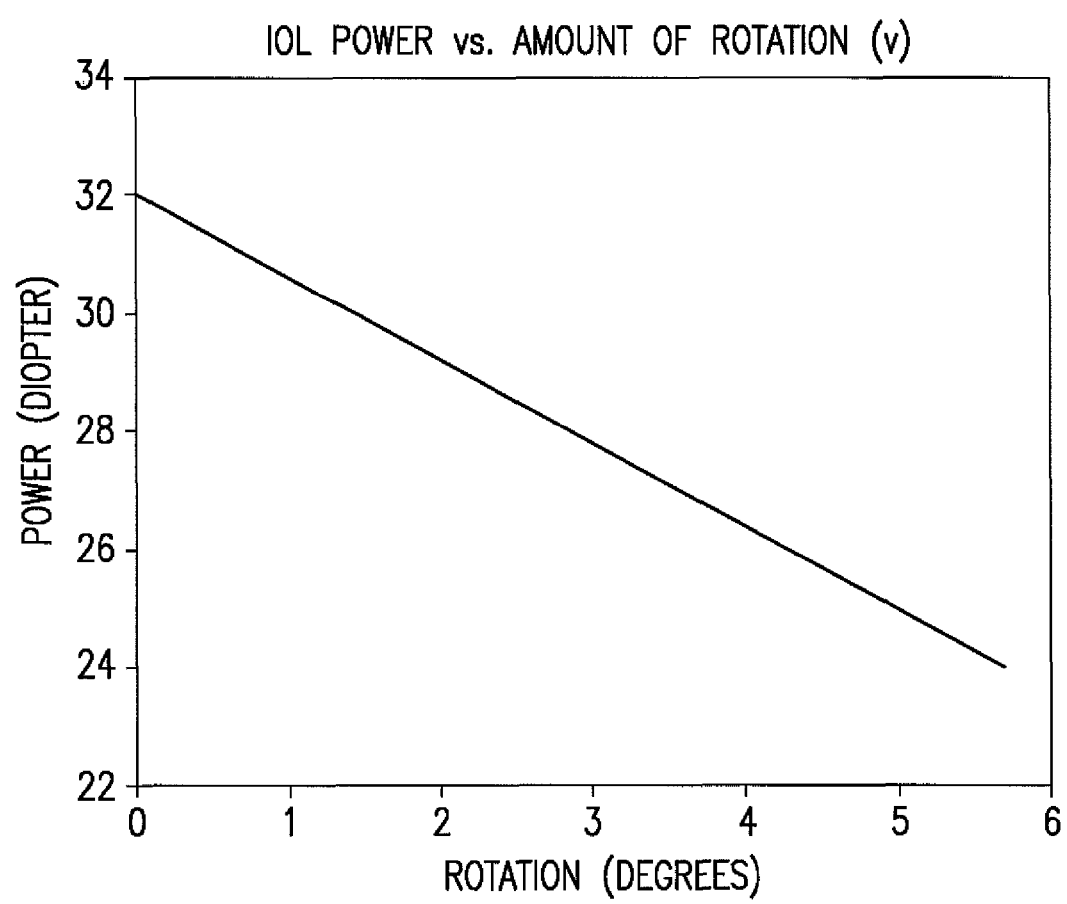
FIG. 14 shows a graph of the simulated lens power vs. the rotation angle of the lenses of a lens system according to an embodiment of the present invention.
Figure 15:
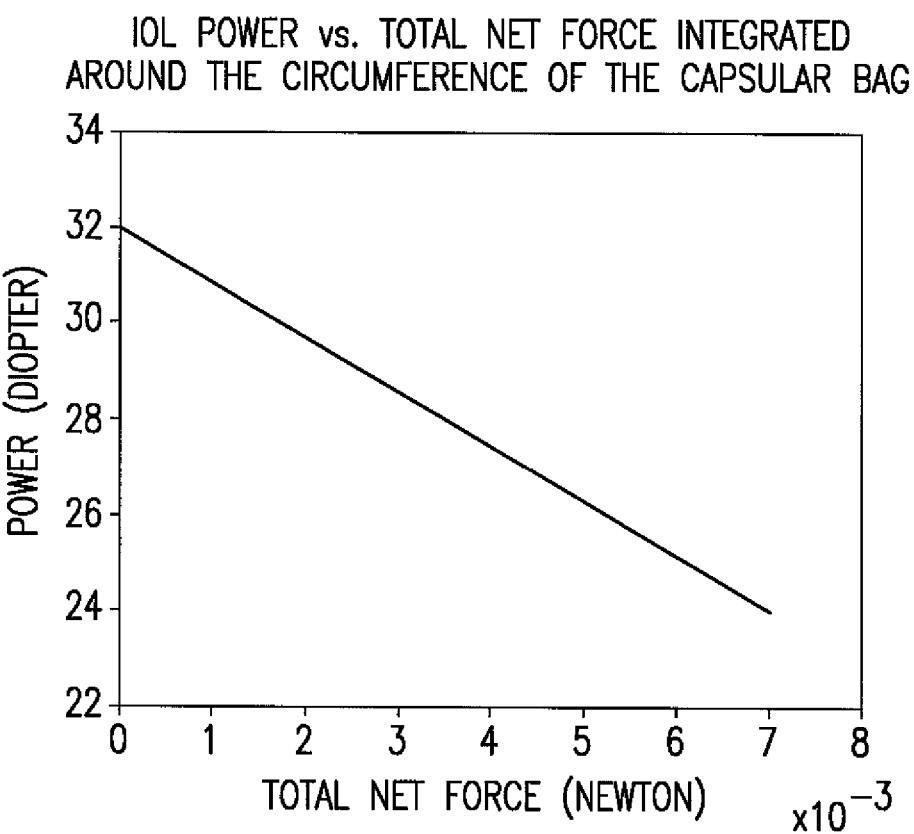
FIG. 15 shows a graph of the simulated lens power vs. the exerted force on the lenses by the ciliary muscle of a lens system according to an embodiment of the present invention.
Figure 16:
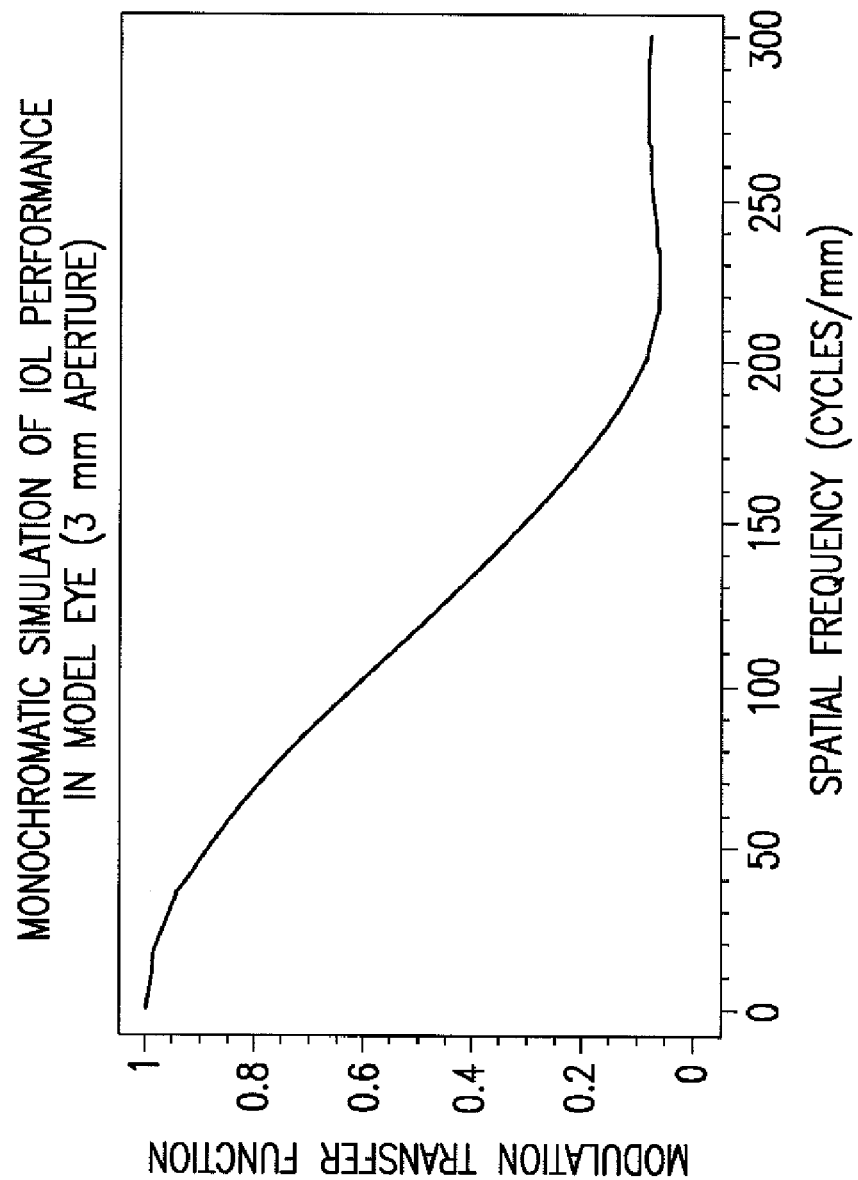
FIG. 16 shows a graph of the simulated modulation transfer function of a lens system according to an embodiment of the present invention.

FIGS. 14, 15 and 16 show the results of simulations, using commercially available ray-tracing and finite-element modelling software packets, of an IOL 21 according to the embodiment of FIGS. 7-8 of the present invention. The simulated optical system consisted of two varifocal lenses shaped according to Eqs. (11)-(14) and using the values of Tables 1 and 2 supra.

FIG. 14 shows that indeed a substantially linear relation may be achieved between the relative rotation of the lenses and the resulting focal power. From the results shown in the plot in FIG. 14, it is seen that the IOL 21 provides a change in optical power of about 1.4 Diopters per degree of rotation, for example, for a nominal lens power of about 28 Diopters. This corresponds to about a 25 percent change in lens power per degree of rotation.

FIG. 15 shows the result of modelling the effect of the net force exerted by the zonulae on the capsular bag, integrated around the circumference of the equatorial rim on the focal power of the IOL 21. The linear behaviour of FIG. 15 is the result of the fact that the entire IOL effectively acts as a single resilient element with a single effective spring constant of the system $C_s$. Thus, the displacement of the lenses, and thus the optical power change, is also linear with the force F exerted on the system, according to the spring equation $F = -C_s U$, wherein U is the amplitude of the extension (positive sign) or compression (negative sign) of the spring.

For this simulation the spring constant of the system is set to $C_s = 70$ mN/rad $= 12.3$ mN/° rotation per lens or $C_s = 242$ mN/mm displacement per lens, relative to the frame. A stiffer IOL may have a higher spring constant $C_s$, e.g. approx. 0.08 N/(full accommodation) which is considered a suitable value for use in a human eye. The spring constant may be set by the material properties and the dimensions of the IOL or particular elements thereof. The resiliency of the capsular bag may be neglected.

The approximation of a constant value for the effective spring constant of the entire system of frame 22 and optical system 23 is valid in the region of elastically deforming and freely movable optical elements, thus as long as the lenses 29A, 29B are free from contact with any stops and/or each other.

The actual values for an effective spring constant or other relevant numerical parameters, such as sizes, weights, focal length etc. depend on the materials and structures used.

FIG. 16 shows the resolving power of the simulated compound lens 29 for 0° relative rotation, i.e. for overlapping lenses and the optimum lens power of 32 Dpt. For this, the modulation transfer function of the lenses is calculated. The modulation transfer function is a measure of the resolving power of an optical system observing an array of adjacent parallel sharp-edged black and white stripes with a particular spatial frequency, and is given by $$MTF = (I_{black} - I_{white})/(I_{black} + I_{white}) \quad (18)$$

wherein $I_X$ is the perceived intensity of the colour "X" at the detector. MTF=1 equals perfect resolving power (individual black and white stripes are crisply detected), MTF=0 equals no resolving power; the array is perceived as a substantially homogeneously grey surface. As may be seen in FIG. 16 the lens performs better than a generally desired benchmark of at least MTF>0.4 for $f_{spatial}$=100 cycles/mm.

Figure 17:
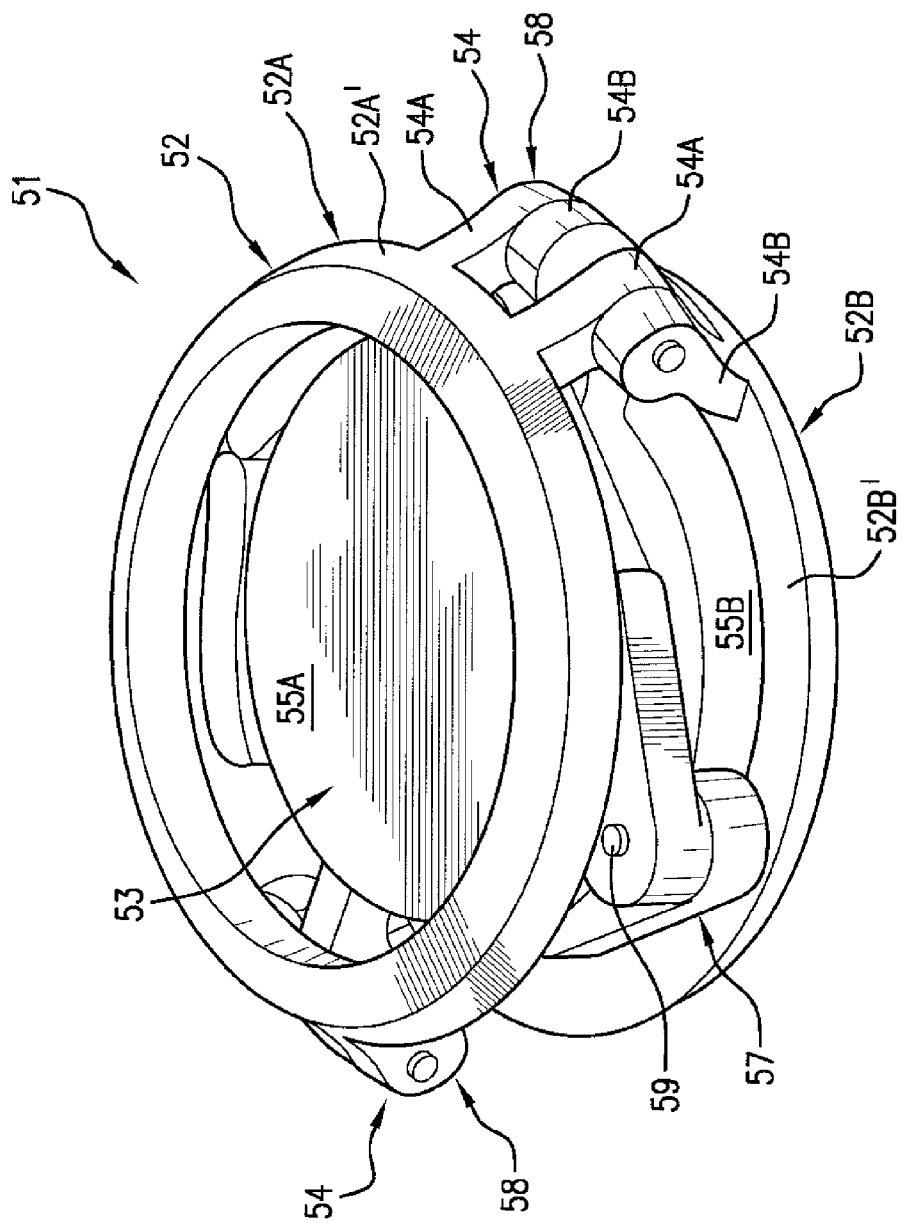
FIG. 17 shows a perspective side view of another embodiment of an intraocular lens according to the present invention.
Figure 18:
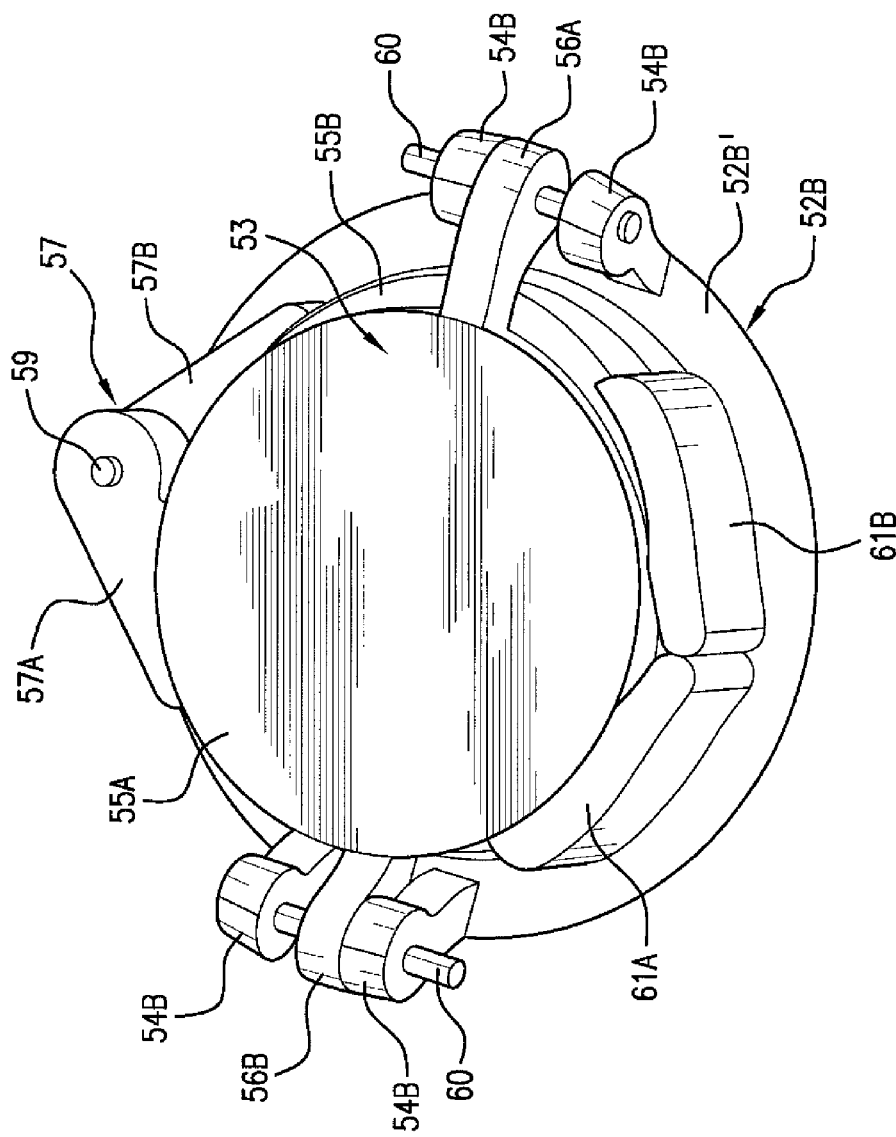
FIG. 18 shows a perspective side view from another angle of the intraocular lens of FIG. 17, with the anterior part removed.

FIGS. 17 and 18 show another embodiment of an IOL, which is similar to that of FIGS. 9-12 in both its basic construction and its functionality. The IOL 51 comprises a frame 52 and an optical system 53. The frame 52 comprises individual frame parts 52A and 52B, comprising an anterior frame element 52A' and a posterior frame element 52B', respectively, and having connecting elements 54. The connecting elements 54 comprise portions 54A, 54B being part of the anterior or posterior frame parts 52A, 52B, respectively. The frame parts 52A and 52B are provided with a central opening and with a relatively sharp edge for hindering cell migration etc. The frame may be sized to remain free from the equatorial rim or to engage it.

The optical system 53 comprises a compound lens 55 in turn comprising two individual varifocal lenses 55A, 55B.

FIG. 18 shows the IOL 51 from another view angle than FIG. 17 and without the upper frame half 52A for clarity.

The lenses 55A, 55B are each attached to a connecting element 54 by a connecting arm 56A, 56B. The lenses 55A, 55B are mutually rotatingly attached to each other by arms 57A, 57B at an interconnection joint 57.

As in the embodiments described above, the frame 52 is arranged for converting a first displacement of the anterior and posterior frame elements 52A', 52B' essentially towards or away from each other, and thus towards or away from the centre of the frame 52, into a second displacement of (the joints 58 of) the connecting elements 54 having at least a component perpendicular to the first displacement, towards or away from the centre of the frame 52.

Figure 19:
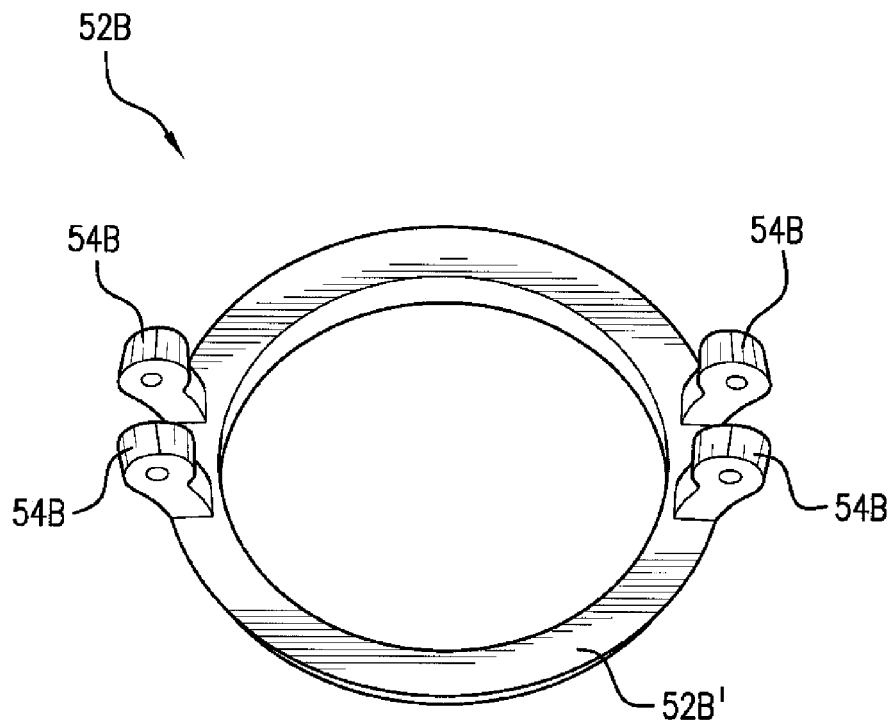
FIGS. 19 and 20 show constituent parts of the embodiment of FIG. 17.
Figure 20:
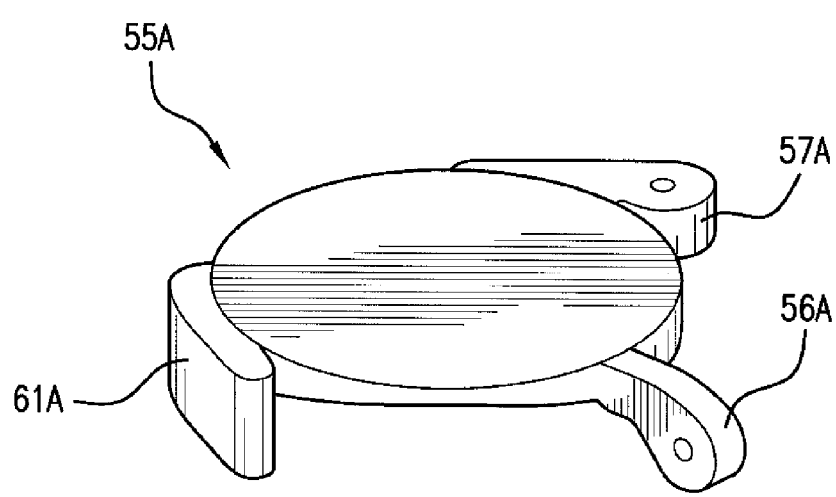

For the IOL 51 the parts 52A, 52B, 55A, 55B are formed individually as shown in FIGS. 19 and 20, respectively and the parts 52A, 52B and 55A, 55B may be substantially identical. Thus, the IOL 51 is essentially modular. This facilitates manufacturing of the IOL 51, since relatively simple molds may be used, which may also facilitate separation, of the mold and the molded part. Parts may be assessed for quality individually and parts may be readily adapted and/or exchanged.

It also facilitates using different materials for parts of the frame 52 and/or of the optical system 53.

For forming an IOL 51, the parts 52A, 52B, 55A, 55B are assembled by means of the joints 57, 58, which may be freely pivotably hinging to essentially rigid, e.g. glued, riveted, or of the peg-in-hole type (cf. joint 33 of FIGS. 9-12), etc. The joints may also be snap-fitting joints, wherein one part is provided with a portion, such as a clamp or a recess, for receiving a corresponding portion, e.g. an extension or a protrusion, of another part. The movability of the joints 57, 58 and the resiliency of (portions of) the parts determines the spring constant of the frame 52, the optical system 53 and thus the IOL 51 as a whole; the connecting element parts MA, MB and/or the anterior frame element 52A' and posterior frame element 52B' themselves may be the resilient element for urging the anterior and posterior frame elements towards a predetermined axial separation.

Here, the joints 57, 58 are indicated as hinges with a pivot 59, 60, respectively. The frame parts 52A, 52B are rigidly or movably attached to the pivots 60. The lenses 55A, 55B may be movably or rigidly attached to the pivots 59, 60, depending on the resiliency of the arms 56A, 56B, 57A, 57B and/or the torsional resiliency of the pivots 59, 60. The connecting elements 54A, 54B and/or the pivots 60 may be provided with an extension for attaching other objects thereto and/or for forming haptics.

Figure 21A:
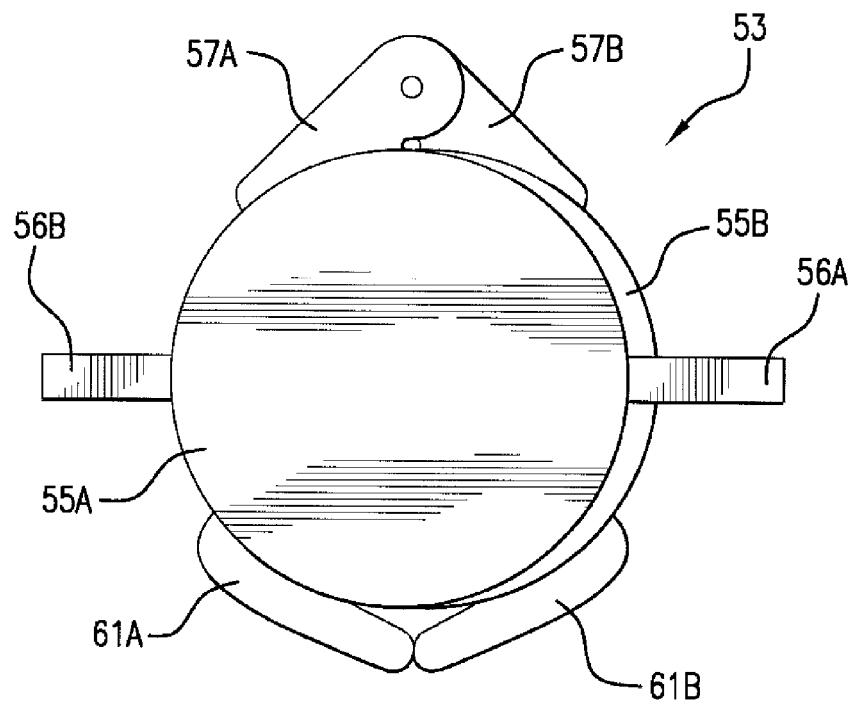
FIGS. 21A and 21B show the operation of the optical system of the embodiment of FIG. 17.
Figure 21B:
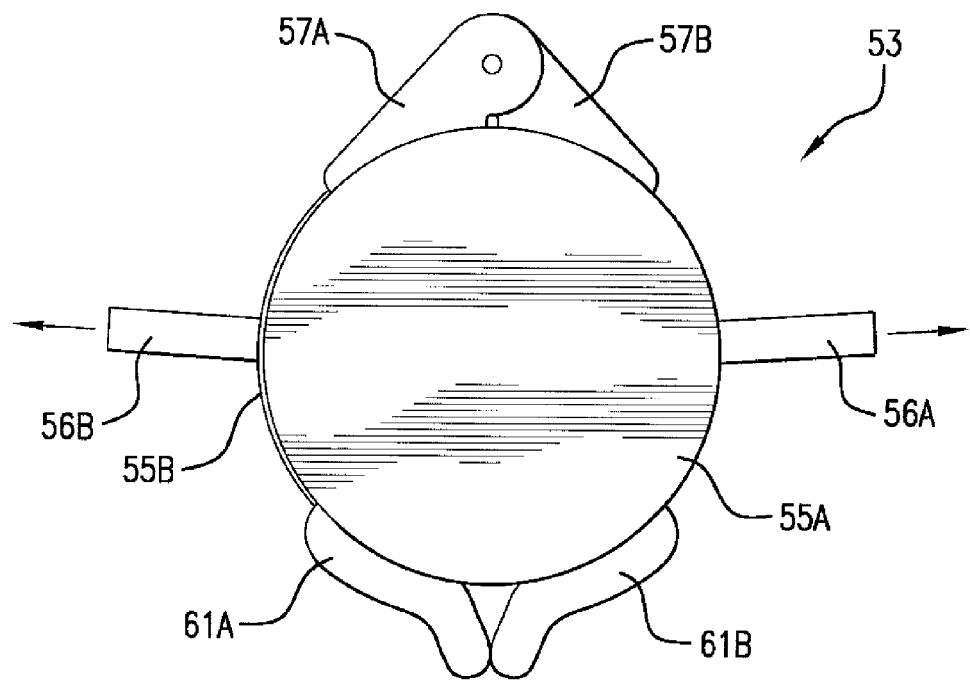

The lenses 55A, 55B are provided with stops 61A, 61B, which each have a resilient extension which is essentially free, not being directly attached to the lenses 55A, 55B (FIGS. 18, 20). These stops serve a double function, as will be explained with reference to FIGS. 21A, 21B, which shows the optical system 53 without the frame 52 in two different positions. The optical system 53 has a default position (FIG. 21A) in which the lenses 55A, 55B are only partially overlapping and the stops just make contact with each other. For changing the focal length of the system, the lenses are pulled (indicated with the arrows in FIG. 21B) to rotate towards fully overlapping and possibly even further (FIG. 21B). Thereby, the resilient extensions of the stops 61A, 61B are urged against each other, causing them to deflect and to provide a restoring force for the optical system 53 and thus for the entire IOL 51 towards the default position (FIG. 21A). Since in this embodiment the pulling force is essentially along a heart line of the optical system 53, the arms 56A, 56B may flex somewhat between the position shifts (FIGS. 21A, 21B). This may cause an additional restoring force for the optical system 53.

The optical system 53 and the stops 61A, 61B may also be sized and designed for a default position with the lenses 55A, 55B essentially fully overlapping and such that the lenses 55A, 55B should be moved away from each other for changing the effective focal length of the compound lens 55.

Figure 22A:
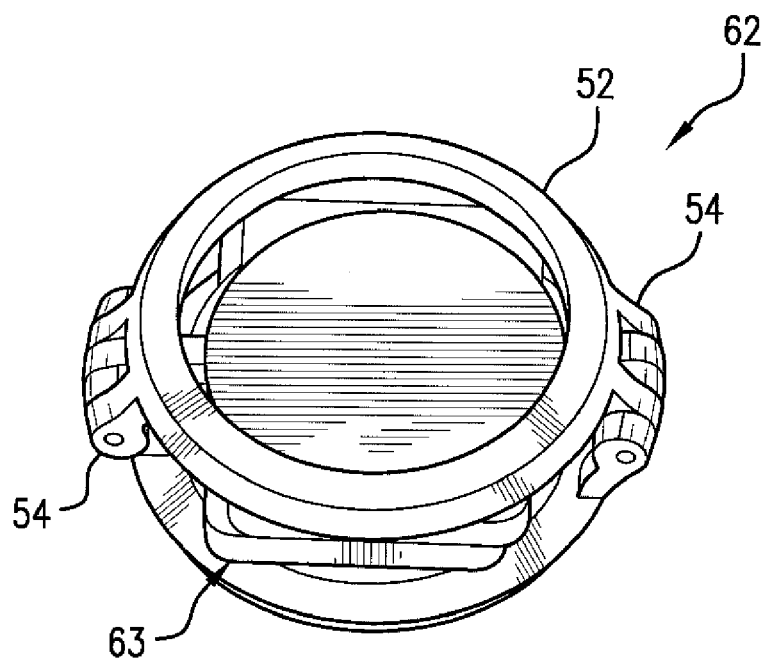
FIGS. 22A and 22B show perspective side views of another embodiment of an intraocular lens according to the present invention.
Figure 22B:
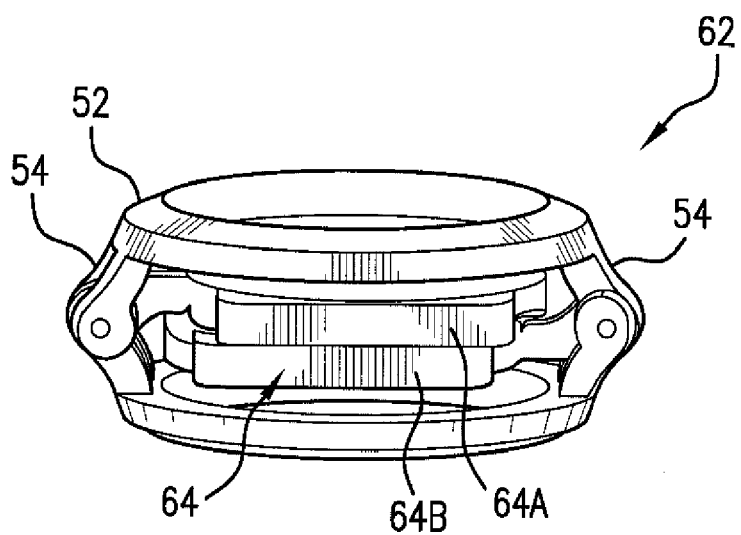
Figure 23:
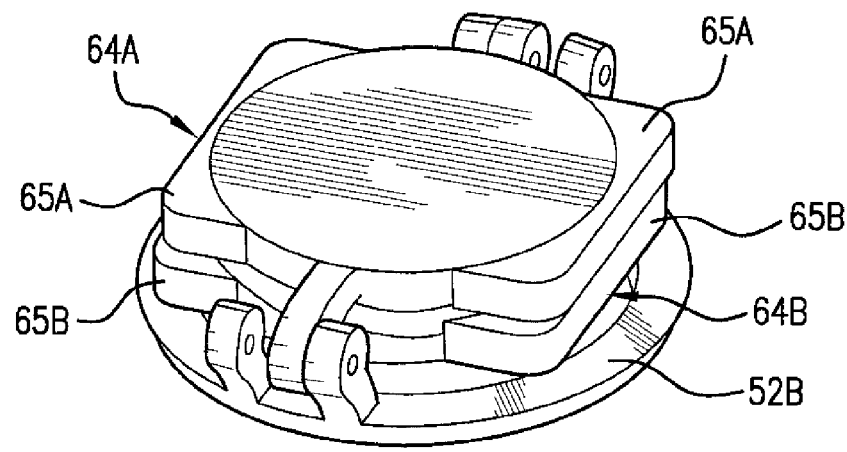
FIG. 23 shows a perspective side view from another angle of the embodiment of FIGS. 22A, 22B, with the anterior part removed.

FIGS. 22A-23 show an embodiment of an IOL 62 which is similar to FIGS. 17, 18. Here, the same frame 52 is provided with another optical system 63, which comprises a compound lens 64, in turn comprising two individual varifocal lenses 64A, 64B. The compound lens 64 is designed for changing its effective focal length upon an essentially linear relative repositioning of the lenses 64A, 64B, rather than upon a relative rotation. For assisting that, the lenses 64A, 64B are provided with extensions 65A, 65B comprising guiding structures which interconnect the lenses 64A, 64B and which define a relative motion path for the lenses 64A, 64B. The displacement is in a direction which is substantially perpendicular to the main optical axis of the lens system axis.

The guiding structures may be formed as one or more protrusions and a matching groove or ribs with facing sliding surfaces, possibly profiled or hooking into each other etc.

Stops and/or end points of the guides may define one or more default relative positions of the lenses 64A, 64B. The lenses 64A, 64B may be essentially identical, allowing to use a single mold for the lenses.

Figure 24:
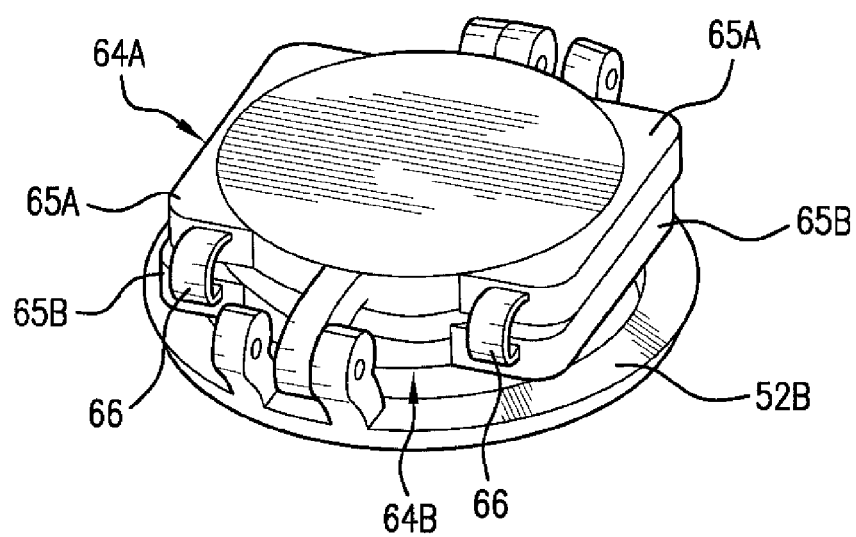
FIG. 24 shows a variant of the embodiment of FIG. 23.

FIG. 24 shows a variant of FIG. 23, wherein the optical system 63 is provided with additional resilient elements 66, e.g. springs, for providing a restoring force towards a default relative position of the lenses 64A, 64B.

The frame 52 may be provided with additional connecting and/or resilient elements. The frame 52 may also be formed or assembled without providing it with an optical system, by just assembling the anterior and posterior frame parts 52A, 52B. Such a frame 52 may be used on its own for biasing the capsular bag 3 towards the accommodating shape, e.g. in combination with filling the capsular bag with a biocompatible material for replacing the natural lens tissue.

Embodiments of the invention are not restricted to those described above herein, but may be varied in a number of ways, for example, as generally expressed by the following claims. For instance, the lenses may have any shape.

The lenses may also be displaced linearly with respect to each other, e.g. by providing lenses with two rotational or resilient interconnections on opposite sides or with a guiding rail etc.

The optical system may also comprise one or more separate optical elements for correcting astigmatism, or elements for correcting other imaging defects, such as coma or chromatic aberration.

The frame may comprise any useful number of resilient and/or connecting elements and/or of optical elements attached thereto. A torsional spring may also be adjustable by means of a reinforcement.

The frame may also be realised or provided with medically active substances, e.g. slow-release ingredients such as medicines.

Elements and aspects of different embodiments may be suitably combined.

What is claimed is:

1. A frame for an intraocular lens, comprising:
   an anterior frame element and a posterior frame element; and
   a connecting element for operably coupling the frame elements to first and second optical elements;
   the connecting element configured to convert a first displacement between the frame elements into a second displacement between the optical elements that is substantially perpendicular to the first displacement.

2. The frame according to claim 1, wherein the connecting element is a resilient element.

3. The frame according to claim 1, wherein the deflection of the connecting element has a radial component with respect to the optical axis of the eye.

4. The frame according to claim 1, wherein at least the anterior frame element provides an opening for allowing aqueous humor to pass therethrough.

5. The frame according to claim 1, whereby at least the posterior frame element is provided with a relatively sharp edge along the contact region of the frame element with the wall of the capsular bag.

6. The frame according to claim 1, further comprising elements for substantially centering the frame about the optical axis of the eye when implanted therein.

7. The frame according to claim 1, wherein the frame is sized for being, once implanted in a capsular bag of an eye, in contact with the interior surface of the capsular bag on the anterior and posterior walls thereof and being free from contact with the equatorial rim thereof.

8. The frame according to claim 1, wherein the net effect of the forces on the capsular bag is to generally urge the capsular bag towards the accommodating shape.

9. An intraocular lens for implantation in the capsular bag of an eye, comprising:
   a frame comprising an anterior frame element and a posterior frame element;
   a first optical element and a second optical element; and
   a connecting element operably coupling the frame elements to the optical elements;
   the connecting element configured to convert a first displacement between the frame elements into a second displacement between the optical elements that is substantially perpendicular to the first displacement.

10. The intraocular lens according to claim 9, wherein one of the optical elements is coupled to a second connecting element of the frame.

11. The intraocular lens according to claim 9, wherein the first and second optical elements are varifocal lenses and the optical elements together have a combined focal length that depends on a rotational and/or linear displacement between the first and second optical elements to one another in a direction that is substantially perpendicular to the optical axis.

12. The intraocular lens according to claim 9, further comprising an interconnection for providing a centre of rotation for at least two individual optical elements with respect to one another.

13. The intraocular lens according to claim 9, further comprising a guide for providing a substantially linear displacement of at least two optical elements with respect to one another.

14. The intraocular lens according to claim 9, wherein the optical elements define a default configuration in which an eye is emmetropic.

15. The intraocular lens according to claim 9, wherein the optical elements define a default configuration in which a capsular bag into which the intraocular lens is placed is in an accommodating shape.

16. The intraocular lens according to claim 9, wherein, when the intraocular lens is placed in a capsular bag of an eye, the resilient element provides a restoring force for urging the optical elements to a default configuration that urges the capsular bag towards an accommodating shape.

17. The intraocular lens according to claim 9, wherein the combination of the first and second lenses have a focal length that is dependent on at least a rotation of the lenses with respect to one another about an axis that is substantially parallel to the optical axis of the lens system.

18. The intraocular lens according to claim 17, wherein the frame is configured to cause the rotation of the lenses, the rotation being due to the natural action of the ciliary muscle on the capsular bag of an eye into which the intraocular lens is implanted.

19. The intraocular lens according to claim 9, wherein the frame has a maximum diameter in a direction perpendicular to the optical axis that is less than 10 mm and, when the frame is in an unstressed state, the spacing along the optical axis between outer portions of the anterior and posterior frame elements is at least 4 mm.

20. The intraocular lens according to claim 9, wherein the frame is sized for contacting the capsular bag of an eye when implanted therein only on the anterior and posterior walls and being free from contact with the equatorial walls.

21. An intraocular lens for implantation in a capsular bag of an eye comprising: a frame disposed about an optical axis; a first optical element and a second optical element; a connecting element operably coupling the frame to the optical elements; a joint disposed about a rotational axis, the optical elements configured to rotate with respect to one another about a rotational axis; wherein the frame and the joint are configured to cause the rotation of the lenses, the rotation being due to the natural action of the ciliary muscle on the capsular bag of the eye into which the intraocular lens is implanted.

22. The intraocular lens of claim 21, wherein the subject is a human subject.

23. The intraocular lens of claim 21, wherein the intraocular lens has a maximum extent in a direction normal to the optical axis that is less than 11 mm.

24. The intraocular lens of claim 21, wherein the distance between the optical axis and the rotational axis is less than 5 mm.

25. The intraocular lens according to claim 21, wherein the rotational axis is substantially parallel to the optical axis.

* * * * *